United States Patent [19]
De Silva et al.

[11] Patent Number: 5,767,363
[45] Date of Patent: Jun. 16, 1998

[54] PLANT PROMOTER INVOLVED IN CONTROLLING LIPID BIOSYNTHESIS IN SEEDS

[75] Inventors: Jacqueline De Silva; Richard Safford. both of Bedford; Stephen Glyn Hughes. Saffron Walden, all of United Kingdom

[73] Assignee: Van den Bergh Foods Company, Division of Conopco, Inc., Lisle, Ill.

[21] Appl. No.: 129,129

[22] PCT Filed: Apr. 8, 1992

[86] PCT No.: PCT/GB92/00627

§ 371 Date: Jan. 18, 1994

§ 102(e) Date: Jan. 18, 1994

[87] PCT Pub. No.: WO92/18634

PCT Pub. Date: Oct. 29, 1992

[30] Foreign Application Priority Data

Apr. 9, 1991 [EP] European Pat. Off. ............ 91303098

[51] Int. Cl.⁶ .................. A01H 4/00; C12N 15/82; C12N 5/14
[52] U.S. Cl. ............... 800/205; 800/255; 800/DIG. 15; 800/DIG. 16; 800/DIG. 17; 435/320.1; 435/172.3; 435/240.4; 435/70.1; 536/24.1
[58] Field of Search .................. 536/24.1; 435/320.1, 435/172.3, 240.4, 70.1; 800/205, 255, DIG. 17, DIG. 15, DIG. 16

[56] References Cited

FOREIGN PATENT DOCUMENTS

| 255377 | 2/1988 | European Pat. Off. |
| 255378 | 2/1988 | European Pat. Off. |

OTHER PUBLICATIONS

WO 91/13980 (Sep. 19, 1991).
WO 91/13972 (Sep. 19, 1991).
WO 91/16421 (Oct. 31, 1991).
WO 92/03564 (Mar. 5, 1992).
De Silva, et al: "The isolation and sequence anyalysis of two seed-expressed acyl carrier protein genes from *Brassica napus*". Plant Molecular Biology: 14: 537–538, 1990.
de Silva, et al J.Exp.Bot. 41 (1990) Supp., p. 5–1.
Knauf: "The application of genetic engineering to oilseed crops". TIBTECH—Feb. 1987, vol. 5, pp. 40–47.
Vanderkerckhove et al: "Enkephalins produced in transgenic plants using modified 2S seed storage proteins". Bio/Technology, vol. 7, Sep. 1989, pp. 929–932.
Bayley, et al: "Metabolic consequences of expression of the medium chain hydrolase gene of the rat in mouse NIH 3I3 cells". Bio/Technology, vol. 6, Oct. 1988, pp. 12191221.
Knauf, et al. Journal of Cellular Biochemistry, Supplement 14E, 1990. UCLA Symposia on Molecular & Cellular Biology, Abstracts—19th Annual Meeting, Mar. 31–Apr. 22, 1990, pp. 257 & 262.

*Primary Examiner*—Che S. Chereskin
*Attorney, Agent, or Firm*—Gerard J. McGowan, Jr.

[57] ABSTRACT

A new seed-specific plant promoter is provided, capable of expressing a gene placed under control of said promoter before or during fatty acid or lipid biosynthesis in plant cells. In nature it occurs in the acyl carrier protein (ACP) gene. This opens the possibility of modifying the fatty acid synthesis in plants, which may result in changing the triacylglycerol composition of oil-containing seeds. Another option is the production of a desired protein in plants, either to improve the nutritional value of the seeds, or for the production of specific proteins that can be isolated from the fruits of plants.

13 Claims, 23 Drawing Sheets

```
001                                                GTCGAC  006
                                                    SalI
CTGCAGCCAG  AAGGATAAAG  AAATTTTGGA  CGCCTGAAGA  AGAGGCAGTT  056
PstI
CTGAGGGAAG  GAGTAAAAGA  GTATGTCTCC  TTAACTCTAC  TATCAAGTTT  106

CAAGAAGCTG  AGCTTGGCTC  TACCTTGATA  TGTTTATTGC  TGTTGTGCAG  156

GTATGGTAAA  TCATGGAAAG  AGATAAAGAA  TGCAAACCCT  GAAGTATTCG  206

CAGAGAGGAC  TGAGGTGAGA  GAGCATGTCA  CTTTTGTGTT  ACTCATCTGA  256

ATTATCTTAT  ATGCGAATTG  TGAGTGGTAC  TAAAAAAGGT  TGTAACTTTT  306

GGTAGGTTGA  TTTGAAGGAT  AAATGGAGGA  ACTTGGTTCG  GTAGCCGTAA  356

CAAGTTTTTG  GGAATCTCTT  GGGTTTTAAA  TTGCTATGGA  GTTTTTTTTT  406

GCCTGCGTGA  CAACATATCA  TCAGCTGTTG  AGAAGGAAGA  TGGTATTAGA  456

AAGGGTCTTT  CTTTCACATT  TTGTGTTGTG  GACAAATATT  AAAGTCAAAT  506

GTGGCACATG  GATTTAATT   CGGCCGGTAT  GGTTTGGTTA  AGACTGGTTT  556

AACATGTATA  ATTAGTCTTT  GTTTTATTTG  GCTCAGCGGT  TTGTTGGTGT  606

TGGTTAGGAA  CTTAGGCTTG  TCTCTTTCTG  ATAAGATCTG  ATTGGTAAGA  656
                                    BglII
TATGGGTACT  GTTTGGTTTA  TATGTTTTGA  CTATTCAGTC  ACTATGGCCC  706

CCATAAATTT  TAATTCGGCT  GGTATGTCTC  GGTTAAGACC  GGTTTGACAT  756

GGTTCATTTC  AGTTCAATTA  TGTGAATCTG  GCACGTGATA  TGTTTACCTT  806

CACACGAACA  TTAGTAATGA  TGGGCTAATT  TAAGACTTAA  CAGCCTAGAA  856

AGGCCCATCT  TATTACGTAA  CGACATCGTT  TAGAGTGCAC  CAAGCTTATA  906
                                                HindIII
AATGACGACG  AGCTACCTCG  GGGCATCACG  CTCTTTGTAC  ACTCCGCCAT  956
```

*Fig. 3* SHEET 1
(CONTINUED ON Fig. 3 SHEET 2)

```
                                                           -51
                                                           Met
CTCTCTCTCC TTCGAGCACA GATCTCTCTC GTGAATATCG ACA ATG        1002
                      BglII
-50                   -45                  -40
Ser Thr Thr Phe Cys Ser Ser Val Ser Met Gln Ala Thr
TCG ACC ACT TTC TGC TCT TCC GTC TCC ATG CAA GCC ACT        1041
SalI
       -36
Ser Leu    1048
TCT CTG    GTATTAGAT CATTTTGCCT CTGATCTGAT TCTTGCTGTT      1086

TGTCACCGTT CAAAACTCTC GACGCATGTT TTGATTATGT TGAGAATTAG     1136

AAAAATGTTA GCTTTACGAA TCTTTAGTGA TCATTTCAAT TGGATTTGCA     1186

ATCCTGTGTG ATCTGTATTC ATTTGATCT GTATTCATTT TGAATCACAA      1236

CTTGCGTGCG AGCTGTAATA GTGTGATTGA GTAGTAGTGT TTTTGAATGA     1286

-35
                         1317     Ala Ala Thr Thr
ACATGTTTTG TTGTATTGAT GGAACAAACA G GCA GCA ACA ACG         1329

-30                -25             Ala       -20
Arg Ile Ser Phe Gln Lys Pro Ala Leu Val Ser Arg Thr
AGG ATT AGT TTC CAG AAG CCA GCT TTG GTT TCA AGG ACT        1368

-15                 -10
Asn Leu Ser Phe Asn Leu Ser Arg Ser Ile Pro Thr Arg
AAT CTC TCC TTC AAT CTA AGC CGT TCA ATC CCC ACT CGC        1407

-5             -1  1
Leu Ser Val Ser Cys Ala     1426
CTC TCA GTC TCC TGC GCG     G TATGTTCTTT TCTAACACCA        1446

CTCTCAGCAT TTGTTTCGAG ATTTCTTAAG TTTTTGTCTA TTTTGGTTTT     1496

2           5          10
    1501    Ala Lys Pro Glu Thr Val Glu Lys Val Ser Lys
    ATTAG   GCC AAA CCA GAG ACA GTT GAG AAA GTG TCT AAG    1534
```

Fig. 3 SHEET 2
(CONTINUED ON Fig. 3 Sheet 3)

|  | 15 |  |  |  |  | 20 |  |  |  | 25 |  |  |
|---|---|---|---|---|---|---|---|---|---|---|---|---|
| Ile | Val | Lys | Lys | Gln | Leu | Ser | Leu | Lys | Asp | Asp | Gln | Asn |
| ATC | GTC | AAG | AAG | CAG | CTA | TCA | CTC | AAA | GAC | GAT | CAA | AAC | 1573

|  |  |  | 30 |  |  |  | 35 |  |  |  |  |
|---|---|---|---|---|---|---|---|---|---|---|---|
| Val | Val | Ala | Glu | Thr | Lys | Phe | Ala | Asp | Leu | Gly | Ala | Asp |
| GTC | GTT | GCG | GAA | ACC | AAA | TTT | GCT | GAT | CTT | GGA | GCA | GAT | 1612

|  | 40 |  | 42 |
|---|---|---|---|
| Ser | Leu | Asp | Thr | 1625
| TCT | CTC | GAC | ACT | GT AATTCACCAA ATGAATCACT CTCTATGTGA 1656

ATTAAACAAC TTGTGTAGTT TTTTTTTTTT TTTTTTTAA TACTGATTAG 1706

|  |  |  | 43 |  | 45 |  |  |  |
|---|---|---|---|---|---|---|---|---|
|  |  | 1726 | Val | Glu | Ile | Val | Met | Gly | Leu |
| ATTGAGTGTT TTGCATGCAG |  | GTT | GAG | ATA | GTG | ATG | GGT | TTA | 1747

| 50 |  |  |  |  | 55 |  |  |  | 60 |  |  |
|---|---|---|---|---|---|---|---|---|---|---|---|
| Glu | Glu | Glu | Phe | His | Ile | Glu | Met | Ala | Glu | Glu | Lys | Ala |
| GAG | GAA | GAG | TTT | CAT | ATC | GAA | ATG | GCT | GAA | GAA | AAA | GCA | 1786

|  | 65 |  |  |  |  | 70 |  |  |  |  | 75 |
|---|---|---|---|---|---|---|---|---|---|---|---|
| Gln | Lys | Ile | Thr | Thr | Val | Glu | Glu | Ala | Ala | Glu | Leu | Ile |
| CAG | AAG | ATC | ACA | ACG | GTG | GAG | GAA | GCT | GCT | GAG | CTC | ATT | 1825

*SstI*

|  |  | 80 |  |  | 83 |  |
|---|---|---|---|---|---|---|
| Asp | Glu | Leu | Val | Gln | Ala | Lys | Lys | *** |
| GAT | GAG | CTC | GTG | CAA | GCC | AAG | AAG | TGACTTT TAGTATTAAG 1866

AGAAGAACCA AAGGCTTTGT TGTTTTCATA ATCTTTCTGT CATTTTCTTT 1916

TATTATGATG TCAAGTCAAG CGACTCTTTG CTAGTAATCT GTATGCCATG 1966

GATCTCTCTC TCTATTTGTC GACTGAAAAC TTTTGGGTTA CACATGAAAG 2016
            *SalI*                                          *HindIII*

CTTTTCTTT TTCTAAAATC CAAAATGAAA GAGTTGTATT AACAGATACA 2066

TAAGTGAAAG AGTAGTCCCT AAGATGACAC TAGCTTCATT TATAAACAAT 2116

CCTATCACAT TGTATATACA GGTTATGATT TATTCCCAAT CAGCGTCAAA 2166

GAATCCAGCA TCTTTCATCT CTGAATAGTA GACATTCTCC AAGTTTAGAT 2216

CTTCCTCCTC GATCAAA 2233

*Fig. 3* SHEET 3

| AP1GUS | LEAF | SEED STAGE 1 | SEED STAGE 2 | SEED STAGE 3 |
|---|---|---|---|---|
| 5 | 3.4 | 10.0 | 187.2 | 551.2 |
| 6 | 5.0 | 68.5 | 99.2 | 249.6 |
| 10 | 2.4 | 8.6 | 5.6 | 38.7 |
| 12 | 0.6 | 0.2 | 0.5 | 1.3 |
| 14 | 14.3 | 1.2 | 2.0 | 165.6 |
| 16 | 25.4 | 209.2 | 424.0 | 264.0 |
| 18 | 18.4 | 320.0 | 348.0 | 248.0 |
| 19 | 8.8 | 144.0 | 200.0 | 284.0 |
| 25 | 7.8 | 79.2 | 136.4 | 516.0 |
| 26 | 2.1 | 41.2 | 137.6 | 426.0 |
| 27 | 1.8 | 0.3 | 138.4 | 448.0 |
| 28 | 0.6 | 0.1 | 52.4 | 300.0 |
| 29 | 3.3 | 10.9 | 22.0 | 416.0 |
| AVE | 7.22 | 68.72 | 134.87 | 300.65 |

| cTAK | LEAF | SEED STAGE 1 | SEED STAGE 2 | SEED STAGE 3 |
|---|---|---|---|---|
| 3A | 14.8 | 15.1 | 32.2 | 5.1 |
| 3B | 9.6 | 2.6 | 7.0 | 24.4 |
| 21 | 24.8 | 12.4 | 5.1 | 18.4 |
| 23 | 900.0 | 720.0 | – | 176.0 |
| AVE | 237.3 | 187.5 |  | 56.0 |

Fig. 6

| | | | | |
|---|---|---|---|---|
| CTGCAGCCAG | AAGGATAAAG | AAATTTTGGA | CGCCTGAAGA | AGAGGCAGTT | 50
| *PstI* | | | | |
| CTGAGGGAAG | GAGTAAAAGA | GTATGTCTCC | TTAACTCTAC | TATCAAGTTT | 100
| CAAGAAGCTG | AGCTTGGCTC | TACCTTGATA | TGTTTATTGC | TGTTGTGCAG | 150
| GTATGGTAAA | TCATGGAAAG | AGATAAAGAA | TGCAAACCCT | GAAGTATTCG | 200
| CAGAGAGGAC | TGAGGTGAGA | GAGCATGTCA | CTTTTGTGTT | ACTCATCTGA | 250
| ATTATCTTAT | ATGCGAATTG | TGAGTGGTAC | TAAAAAAGGT | TGTAACTTTT | 300
| GGTAGGTTGA | TTTGAAGGAT | AAATGGAGGA | ACTTGGTTCG | GTAGCCGTAA | 350
| CAAGTTTTTG | GGAATCTCTT | GGGTTTTAAA | TTGCTATGGA | GTTTTTTTT | 400
| GCCTGCGTGA | CAACATATCA | TCAGCTGTTG | AGAAGGAAGA | TGGTATTAGA | 450
| AAGGGTCTTT | CTTTCACATT | TTGTGTTGTG | GACAAATATT | AAAGTCAAAT | 500
| GTGGCACATG | GATTTTAATT | CGGCCGGTAT | GGTTTGGTTA | AGACTGGTTT | 550
| AACATGTATA | ATTAGTCTTT | GTTTTATTTG | GCTCAGCGGT | TGTTGGTGT | 600
| TGGTTAGGAA | CTTAGGCTTG | TCTCTTTCTG | ATAAGATCTG | ATTGGTAAGA | 650
| | | | *BglII* | |
| TATGGGTACT | GTTTGGTTTA | TATGTTTTGA | CTATTCAGTC | ACTATGGCCC | 700
| CCATAAATTT | TAATTCGGCT | GGTATGTCTC | GGTTAAGACC | GGTTTGACAT | 750
| GGTTCATTTC | AGTTCAATTA | TGTGAATCTG | GCACGTGATA | TGTTTACCTT | 800
| CACACGAACA | TTAGTAATGA | TGGGCTAATT | TAAGACTTAA | CAGCCTAGAA | 850
| AGGCCCATCT | TATTACGTAA | CGACATCGTT | TAGAGTGCAC | CAAGCTTATA | 900
| | | | | *HindIII* |
| AATGACGACG | AGCTACCTCG | GGGCATCACG | CTCTTTGTAC | ACTCCGCCAT | 950

*Fig. 16* SHEET 1
(CONTINUED ON Fig.16 SHEET 2)

```
                                                              -51
                                                              Met
      CTCTCTCTCC TTCGAGCACA GATCTCTCT CGTGAATAACG AAA ATG          996
                            BglII
      -50                        -45                   -40
      Ala Thr Thr Phe Ser Ala Ser Val Ser Met Gln Ala Thr
      GCG ACC ACT TTC AGC GCT TCA GTC TCC ATG CAA GCT ACC         1035

-35                     -30                 -25
      Ser Leu Val Thr Thr Thr Arg Ile Ser Phe Gln Lys Pro
      TCT CTG GTC ACA ACA ACG AGG ATT AGT TTC CAA AAG CCA         1074

-20                 -15
      Val Leu Val Ser Asn His Gly Arg Thr Asn Leu Ser Phe
      GTT TTG GTT TCC AAC CAT GGA AGG ACT AAT CTC TCC TTC         1113

-10                     -5                  -1   1
      Asn Leu Ser Arg Thr Arg Leu Ser Ile Ser Cys Ala Ala
      AAC CTA AGC CGC ACT CGC CTT TCA ATC TCT TGC GCG GCA         1152

5                      10                  15
      Glu Thr Ala Val Asn Ala Lys Ser Pro Arg Asn Glu Lys
      GAG ACA GCA GTC AAT GCT AAG AGT CCC AGG AAT GAA AAG         1191

20                  25
      Val Leu Asn Cys Leu Tyr Gln Asn Pro Asp Ala Val Phe
      GTT TTG AAC TGT TTG TAT CAA AAT CCT GAT GCA GTT TTC         1230

30                      35                  40
      Lys Leu Ile Cys Phe Pro Trp Ala Gly Gly Gly Ser Ile
      AAG CTG ATC TGC TTC CCT TGG GCA GGA GGC GGC TCC ATC         1269

45                  50
      His Phe Ala Lys Trp Gly Gln Lys Ile Asn Asp Ser Leu
      CAT TTT GCC AAG TGG GGC CAA AAG ATT AAC GAC TCT CTG         1308

55                      60                  65
      Glu Val His Ala Val Arg Leu Ala Gly Arg Glu Thr Arg
      GAA GTG CAT GCT GTA AGA CTG GCT GGA AGA GAA ACC CGA         1347
```

*Fig. 16* SHEET 2
(CONTINUED ON Fig. 16 SHEET 3)

```
                    70                        75                        80
    Leu Gly Glu Pro Phe Ala Asn Asp Ile Tyr Gln Ile Ala
    CTT GGA GAA CCT TTC GCA AAT GAC ATC TAC CAG ATA GCT        1386

85                        90
    Asp Glu Ile Val Thr Ala Leu Leu Pro Ile Ile Gln Asp
    GAT GAA ATC GTG ACC GCC CTG TTG CCC ATC ATT CAG GAT        1425

95                       100                       105
    Lys Ala Phe Ala Phe Phe Gly His Ser Phe Gly Ser Tyr
    AAA GCT TTT GCG TTT TTT GGC CAC AGT TTT GGA TCC TAC        1464

110                       115
    Thr Ala Leu Ile Thr Ala Leu Leu Leu Lys Glu Lys Tyr
    ACT GCT CTT ATT ACT GCT CTG CTC CTA AAG GAG AAA TAC        1503

120                      125                       130
    Lys Met Glu Pro Leu His Ile Phe Val Ser Gly Ala Ser
    AAA ATG GAG CCG CTG CAT ATT TTT GTA TCC GGT GCA TCC        1542

135                       140                      145
    Ala Pro His Ser Thr Ser Arg Pro Gln Val Pro Asp Leu
    GCC CCT CAC TCA ACA TCC CGG CCT CAA GTT CCT GAT CTT        1581

150                       155
    Asn Glu Leu Thr Glu Glu Gln Val Arg His His Leu Leu
    AAC GAA TTG ACA GAA GAA CAA GTC AGA CAT CAC CTT CTG        1620

160                       165                      170
    Asp Phe Gly Gly Thr Pro Lys His Leu Ile Glu Asp Gln
    GAT TTC GGA GGC ACG CCC AAG CAT CTC ATA GAA GAC CAG        1659

175                       180
    Asp Val Leu Arg Met Phe Ile Pro Leu Leu Lys Ala Asp
    GAT GTT CTG AGG ATG TTC ATT CCT TTG CTG AAG GCA GAT        1698

185                      190                       195
    Ala Gly Val Val Lys Lys Phe Ile Phe Asp Lys Pro Ser
    GCT GGC GTT GTG AAA AAA TTC ATC TTT GAC AAG CCC TCC        1737
```

*Fig. 16* SHEET 3
(CONTINUED ON Fig. 16 SHEET 4)

```
              200                    205                      210
Lys Ala Leu Leu Ser Leu Asp Ile Thr Gly Phe Leu Gly
AAA GCT CTT CTC TCT CTG GAC ATA ACG GGC TTC CTT GGA      1776

215                    220
Ser Glu Asp Thr Ile Lys Asp Ile Glu Gly Trp Gln Asp
TCT GAA GAT ACA ATA AAG GAC ATA GAA GGC TGG CAA GAC      1815

225                      230                     235
Leu Thr Ser Gly Lys Phe Asp Val His Met Leu Pro Gly
CTA ACC AGT GGG AAG TTT GAT GTC CAC ATG CTG CCA GGC      1854

240                    245
Asp His Phe Tyr Leu Met Lys Pro Asp Asn Glu Asn Phe
GAC CAC TTT TAT CTG ATG AAG CCC GAC AAC GAG AAC TTT      1893

250                      255                      260
Ile Lys Asn Tyr Ile Ala Lys Cys Leu Glu Leu Ser Ser
ATC AAG AAC TAC ATA GCC AAG TGC TTG GAA CTC TCG TCA      1932

264
Leu Thr ***
CTC ACT TGA   CTACTTTTA GATGAGCTTT CTTTGGGGCT            1970

GTGGATATGC AGACGGTTCA AAAGCTGCTC CTCTGGGTCC AGATC         2015
                                              BglII
```

Fig. 16 SHEET 4

PLANT PROMOTER INVOLVED IN CONTROLLING LIPID BIOSYNTHESIS IN SEEDS

BACKGROUND OF THE INVENTION

The invention relates to transforming plant cells for modifying the seed-specific production of fatty acids resulting in a changed fatty acid composition of seed oils. In particular the invention provides a new promoter isolated from a seed-specific acyl carrier protein (ACP) gene present in *Brassica napus* (oil seed rape).

During the last decade methods have been developed for transforming plants by introducing genes into plants which on expression give new or improved properties to the resulting transformed plants. One of these methods is the use of the bacterium *Agrobacterium tumefaciens* for introducing the desired gene into the chromosome of the plant to be transformed. Many articles have been published on this technique. For a general introduction reference is made to Chapter 13 (Genetic Engineering of Plants by Using Crown Gall Plasmids) on pages 164–175 of the book 'Recombinant DNA, A Short Course' by James D. Watson, John Tooze and David T. Kurtz, published by Scientific American Books in 1983 and distributed by W. H. Freeman and Company, New York, U.S.A.

According to European patent specification EP-A2-0255378 (CALGENE, INC.), published on 3 Feb. 1988 with claimed priority date of 31 Jul. 1986, a so-called transcriptional initiation region of the napin gene is identified and isolated from plant cells, and used to prepare expression cassettes which may then be inserted into plant cells for seed specific transcription. It is stated in that patent specification that the method may be applied in conjunction with modifying fatty acid production in seed tissue.

From that EP-A-0255378 the following passages are quoted:

on page 3, lines 6–9:

"Transcriptional initiation regions of particular interest are those associated with the Brassica napus or campestris napin genes, acyl carrier proteins, genes that express from about day 7 to day 40 in seed, particularly having maximum expression from about day 10 to about day 20, where the expressed gene is not found in leaves, while the expressed product is found in seed in high abundance."

on page 4, lines 11–22:

"The constructs may be used . . . to modify the fatty acid composition in seeds, that is changing the ratio and/or amounts of the various fatty acids, as to length, unsaturation, or the like . . . . These results can be achieved by providing for reduction of expression of one or more endogenous products, particularly enzymes or cofactors, by producing a transcription product which is complementary to the transcription product of a native gene, so as to inhibit the maturation and/or expression of the transcription product, or providing for expression of a gene, either endogenous or exogenous, associated with fatty acid synthesis. Expression products associated with fatty acid synthesis include acyl carrier protein, thioesterase, acetyl transacylase, acetyl-coA carboxylase[m], ketoacyl-synthases, malonyl transacylase, stearoyl-ACP desaturase, and other desaturase enzymes."

on page 4, lines 57–64:

"Expression cassettes of particular interest include transcriptional regions from napin genes, particularly Brassica napin genes, more particularly *Brassica napus* or *Brassica campestris* genes, regulating structural genes associated with lipid production, particularly fatty acid production, including acyl carrier proteins, which may be endogenous or exogenous to the particular plant, such as spinach acyl carrier protein, Brassica acyl carrier protein, acyl carrier protein, either napus or campestris, Cuphea acyl carrier protein, acetyl transacylase, malonyl transacylase, β-ketoacyl synthases I and II, thioesterase, particularly thio esterase II, from plant, mammalian, or bacterial sources, for example rat thioesterase II, acyl ACP, or phospholipid acyl desaturases."

It should be noted that the time periods indicated in the passage quoted from page 3, lines 6–9, sometimes mentioned as Days After Flowering (DAF) is not always a precise unit, because for the same plants it can differ depending on the location and conditions of growth. Thus, DAF should not be used as an absolute but as a comparative parameter. Therefore, when comparing results of this nature from experiments done at different times or different locations, one has to be particularly careful in drawing conclusions on the basis of differences in DAF values.

Furthermore, with experiments in tobacco the rate of development of individual seed pods even on a single plant may be variable, i.e. the earliest pods developing fastest, in which case it is not possible with tobacco to use DAF for determining accurately the developmental stage of a seed. In such a situation seeds have to be staged using morphological characteristics. This is expanded later on in this specification (see Example 1.c.5 and Example 3, experiment 2). Example I of EP-A-0255378 discloses a construct comprising the structural gene encoding spinach leaf acyl carrier protein under control of the napin promoter from *B. napus*. No evidence was given that the protein was formed: by means of Northern blots only the presence of the corresponding mRNA was made plausible in embryos but not in leaves indicating seed-specific expression of the spinach leaf ACP gene.

Example II discloses construction of a *B. campestris* napin promoter cassette. It was only suggested that a gene involved in the fatty acid synthesis might be inserted into that cassette. No experimental details on such insertion or expression of such gene were given.

According to Example III:

"Other seed-specific promoters may be isolated from genes encoding proteins involved in seed triacylglycerol synthesis, such as acyl carrier protein from Brassica seeds. Immature seed[s] were collected from *Brassica campestris* cv."R-500," a self-compatible variety of turnip rape. Whole seeds were collected at stages corresponding approximately to 14 to 28 days after flowering . . . preparation of a cDNA bank . . . . To probe the cDNA bank, the oligonucleotide . . . was synthesized . . . . This synthetic DNA molecule will hybridize at low stringencies to DNA or RNA sequences coding for the amino acid sequence (ala-ala-lys-pro-glu-thr-val-glu-lys-val). This amino acid sequence has been reported for ACP isolated from seeds of *Brassica napus* (A. R. Slabas et al., 7th International Symposium of the Structure and Function of Plant lipids, University of California, Davis, Calif., 1986); ACP from *B. campestris* seed is highly homologous . . . . DNA sequence analysis of two DNA clones showing obvious hybridization to the oligonucleotide probe indicated that one, designated pCGN1Bcs, indeed coded for an ACP-precursor protein by the considerable homology of the encoded amino acid sequence with ACP proteins described from *Brassica napus* (A. R. Slabas et al., 198[6] supra). Similarly to Example II, the ACP cDNA clone can be used to isolate a genomic clone from which an expression cassette can be fashioned in a manner directly analogous to the *B. campestris* napin cassette.38

Under the next heading Other Examples it was stated:

"Ninety-six clones from the 14–28 day post-anthesis *B. campestris* seed CDNA library (described in the previous example) were screened. . . . Other seed-specific genes may also serve as useful sources of promoters . . . . Without knowing their specific functions, yet other cDNA clones can be classified as to their level of expression in seed tissues, their timing of expression (i.e., when post-anthesis they are expressed) . . . . Clones fitting the criteria necessary for expressing genes relating to fatty acid synthesis or other seed functions can be used to screen a genomic library for genomic clones which contain the 5' and 3' regulatory regions necessary for expression. The non-coding regulatory regions can be manipulated to make a tissue-specific expression cassette in the general manner described for the napin genes in previous examples.

One example of a cDNA clone is EA9. It is highly expressed in seeds and not leaves from *B. campestris* . . . . Northern blot analysis of mRNA isolated from day 14 seed, and day 21 and 28 post-anthesis embryos using a 700 bp EcoRI fragment of EA9 as a probe shows that EA9 is highly expressed at day 14 and expressed at a much lower level at day 21 and day 28 . . . . The partial sequence provided here for clone EA9 (FIG. 3) can be used to synthesize a probe which will identify a unique class of Brassica seed-specific promoters."

In related European patent specification EP-A2-0255377 (CALGENE, INC.), also published on 3 Feb. 1988 with claimed priority date of 31 July 1986, the DNA sequences of structural genes encoding ACP of spinach and *Brassica campestris* are provided, which can be used for production of ACPs as an end product or may enhance seed oil production in plant seed. Also described are napin promoters of *B. napus* and *B. campestris* substantially limiting expression of the ACP genes to seed tissue, which promoters are the same as described in EP-A2-0255378.

However, according to M. A. Post-Beittenmiller et al. in The Plant Cell 1 (1989) 889–899 no significant alterations in leaf lipid biosynthesis were detected by lipid analysis, neither in level nor in composition, when tobacco was transformed with a chimaeric gene consisting of the tobacco ribulose-1,5-biphosphate carboxylase promoter and transit peptide and the sequence encoding mature spinach ACP-I. They further showed that the mature spinach ACP-I gene was expressed at higher levels than the endogenous tobacco ACPs as shown by protein immunoblols. Thus this later work shows that increased production of ACP in plant tissue need not necessarily result in an altered fatty acid composition.

This finding is in agreement with statements made by V. C. Knauf in "The application of genetic engineering to oilseed crops" published in TIBTECH 5 (February 1987) 40–47, in which he mentioned many possibilities why "a 'typical' project" for altering the fatty acid composition of rape seed might fail due to the complexity of lipid biosynthesis in plant tissues.

In a paper entitled "Plastid-localised seed acyl-carrier protein of *Brassica napus* is encoded by a distinct, nuclear multigene family " R. Safford et al. provide in Eur. J. Biochem. 174 (1988) 287–295 the first insight into the origin, structure and expression of genes co-ordinating fatty acid biosynthesis in oil-bearing seeds. It reveals seed ACP to be localised within plastid bodies and to be encoded in nuclear DNA, being synthesised as a precursor containing an N-terminal extension sequence which presumably directs import of the protein into the plastids. Analysis of several cDNA clones revealed sequence heterogeneity and thus evidence for an ACP multigene family. Further experiments showed that at least some of these genes were not expressed in leaf tissue. In FIG. 8A of this publication not more than 56 nucleotides of the 5'-non-coding regions upstream of the ACP start codon are given. The promoters could not be determined because the work was done with cDNA clones from mRNA as starting material, which contains only transcribed sequences, instead of chromosomal DNA, the latter containing transcription regulating sequences including the promoter region.

In a subsequent paper of J. de Silva et al. in Plant Molecular Biology 14 (1990) 537–548 the same group described the isolation and sequence analysis of two genomic clones encoding seed-expressed acyl carrier protein genes from *Brassica napus*. The latter paper discloses that the transcription start site is situated 69 bp upstream of the (ATG) start-codon of the structural gene.

Thus, the 5' regions shown in both papers are less than 70 nucleotides long and describe the DNA sequences downstream of the transcription start site. Therefore, they neither comprise a promoter region nor a regulatory region conferring seed-specific temporal regulation of gene transcription.

Summarizing the prior art, EP-A-0255378 describes the isolation and use of napin promoters of *B. napus* and *B campestris* and suggests how other promoters like the ACP promoters can be isolated, EP-A-0255377 describes the same napin promoters, and the R. Safford et al. (1988) and the J. de Silva et al. (1990) publications describe only less than 70 nucleotides of the 5' region preceding the structural gene encoding the seed-specific ACP of *B. napus*, so that neither of these publications discloses the nucleotide sequence of an ACP promoter.

SUMMARY OF THE INVENTION

The invention provides a novel seed-specific ACP promoter isolated from *Brassica napus* and DNA constructs which can be employed in manipulating plant cells to provide for seed-specific transcription.

According to one embodiment of the invention, a desired gene encoding a protein active in the biosynthetic pathway for fatty acid production is placed under control of the novel ACP promoter and introduced into plant genomes to provide for seed-specific transcription, whereby the gene may be homologous or heterologous to the plant genome. The constructs provide for modulation of endogenous products or of their production, as well as for production of heterologous products. In order to be capable of influencing the fatty acid biosynthesis the protein to be produced must be targeted to the correct intracellular site of the cell, i.e. the plastids. This requires that a chimaeric DNA construct be made, in which the desired gene is linked to a suitable transit sequence such that the resulting chimaeric protein will be targeted to the plastid, thus enabling release of the mature form of the protein corresponding to the desired gene within the plastid. Some examples of proteins active in the biosynthetic pathway for fatty acid production are acetyl-coA carboxylases, acetyl transacylases, ACPS, desaturases, elongases, enoyl-reductases, β-keto-reductases, ketoacyl-synthases, malonyl transacylases, and thioesterases.

According to another embodiment of the invention a gene encoding a desired protein is placed under control of the novel ACP promoter. Such a desired protein can be any protein the production of which in plants and, optionally its subsequent isolation, is desirable. As examples of such proteins can be mentioned (1) enzymes to be used in food processing, e.g. guar α-galactosidase, thaumatin, chymosin, (2) proteins that can inhibit the formation of anti-nutritive factors, (3) pharmaceutically active proteins, e.g. blood factors, interferon, hormones, human serum albumin, and (4) plant proteins with a more desirable amino acid composition, e.g. one with a higher lysine content than occurring in the non-transformed plant.

Depending on the influence of the desired protein on the cell metabolism it can be allowed to reside in the cytoplasm, or it can be targeted to the plastids, in which case the gene encoding the desired protein should be linked to a target sequence as described above. Alternatively it can be targeted to other organelles within the cell, for which other targeting sequences are required. Several other targeting sequences are described before; see for example G. Van den Broek et al. in Nature 313 (31 Jan. 1985) 358–363 on targeting of a foreign protein to chloroplasts, and a review on protein targeting by R. J. Ellis & C. Robinson in Advances in Botanical Research 14 (1987/8) 1–24 published by Academic Press Ltd. (ISBN 0-12-005914-2) showing targeting to the chloroplasts, the mitochondria and the nucleus of plants.

DESCRIPTION OF THE SPECIFIC EMBODIMENTS

The present invention is based upon carrying out research on the factors which may influence the expression of a protein involved in the fatty acid synthesis in the seeds of plants like Brassica napus. This research was needed in a project directed to changing the fatty acid profile of seed oils such as rape. In order to change the fatty acid composition of a storage lipid in plants or to induce production of a desired polypeptide or protein in seeds of a plant by means of genetical engineering, the expression of the relevant genes has to be controlled in the following manner:

i) The expression of the desired gene should be confined to seed tissue only, at the correct developmental stage and at an appropriate level.

ii) Specifically in the case of modifying the fatty acid profile of the seed lipids:

a) Transport of the resulting protein into the fatty acid synthesizing sub-compartment of the cell (so-called plastid) in a biologically active form, and b) Transportation of synthesized fatty acids out of the plastid and their subsequent conversion to triacylglycerides.

One way to achieve step i) is to utilize a promoter region isolated from an endogenous gene involved in the fatty acid biosynthesis. Such a promoter would activate gene expression before or at the stage that fatty acid biosynthesis in the seed occurs.

To obtain controlled expression of a desired gene in plants, e.g. rape seed, the structural gene can, for example, be placed under control of a promoter region isolated from an endogenous rape seed lipid biosynthetic gene. Although some seed-specific promoters were already known as described above, there have been no reports describing the isolation and functional characterisation of such regulatory DNA sequences of genes involved in the biosynthesis of seed lipids in plants.

An example of one such gene is the gene encoding ACP, which is a key component of the fatty acid biosynthetic machinery of plants, serving as a component of the fatty acid synthetase (FAS) and is also involved in desaturation and acyl transfer reactions (P. K. Stumpf et al. Fatty acid biosynthesis in higher plants. In: Fatty Acid Metabolism and Its Regulation. Elsevier Press, Amsterdam, Numa S. (ed), (1984) 155–179).

In the course of the research resulting in the present invention a promoter was selected belonging to the chromosomal ACP05 gene described by J. de Silva et al. (1990) supra, which corresponds to the ACP-encoding 29CO8 cDNA described earlier by R. Safford et al. (1988) supra. The latter publication showed the isolation and characterisation of cDNA clones encoding rape embryo ACP and that ACP is synthesized as a precursor containing an N-terminal transit sequence. The latter can be used as a 'tool' to transport products of foreign genes into fatty acid synthesising plastids.

Functional analysis of the promoter element present in the 5' upstream region of the ACP gene was carried out using the β-glucuronidase (GUS) reporter gene and tobacco transformation.

A 1.4 kb 5' upstream fragment of rape ACP05 gene (AP1 promoter) was fused to the β-glucuronidase (GUS) reporter gene and transferred, via Agrobacterium infection, into tobacco. Analysis of leaf and seed tissue from 15 transgenic tobacco plants showed the level of GUS expression to increase through seed development to a value that was, on average, approximately 100×higher than that observed in leaf. Analysis of control plants transformed with constructs containing the GUS gene linked to a constitutive plant promoter (CaMV 35S) showed similar levels of GUS expression in leaf and all stages of seed development. These results demonstrate that the isolated AP1 promoter sequence functions to control expression of the GUS gene in transgenic tobacco in the desired seed specific and developmental manner.

In a comparative study with CaMV 35S and AP1 promoters, the level of GUS expression obtained with the AP1 promoter at the stage of maximum seed lipid synthesis was equivalent to that obtained with the powerful plant promoter CaMV 35S. Therefore, the AP1 promoter can be considered as a 'strong', seed-specific promoter. The CaMV 35S promoter itself cannot be used for this purpose, because it is a constitutive promoter that produces the protein throughout the plant, which is undesirable.

In order to define more precisely the essential part of the rape ACP05 promoter, including any specific, developmental regulation sequence(s), a deletion analysis was performed. Chimaeric gene constructs containing 1.4 kb, 0.92 kb and 0.29 kb, respectively, of the region upstream from the transcription initiation start site of the ACP05 gene fused to the β-glucuronidase (GUS) reporter gene were transferred into tobacco. For each construct 10 transformed plants were analysed for mode of GUS expression. No significant differences were observed in either the level or tissue distribution of GUS activity in plants transformed with the 'deleted' versions of the ACP promoter compared to the 'original' 1.4 kb construct. It was therefore concluded that the DNA sequences which determine the level of transcription and seed specificity of the ACP05 gene reside within the 0.29 kb region immediately upstream of the start site of transcription of the gene, which start site was described in the J. de Silva et al. (1990) publication supra.

This DNA fragment was sequenced and the resulting 291 bp DNA sequence (SEQ ID NO:1) is

```
1
AGATCTGATT GGTAAGATAT GGGTACTGTT TGGTTTATAT GTTTTGACTA  50
TTCAGTCACT ATGGCCCCCA TAAATTTTAA TTCGGCTGGT ATGTCTCGGT  100
TAAGACCGGT TTGACATGGT TCATTTCAGT TCAATTATGT GAATCTGGCA  150
CGTGATATGT TTACCTTCAC ACGAACATTA GTAATGATGG GCTAATTTAA  200
GACTTAACAG CCTAGAAAGG CCCATCTTAT TACGTAACGA CATCGTTTAG  250
AGTGCACCAA GCTTATAAAT GACGACGAGC TACCTCGGGG C           291.
```

To compare the temporal regulation of the ACP05 promoter in relation to other seed-specific plant promoters it was determined if the respective promoter elements from the lipid biosynthetic gene (ACP05) and from two storage protein genes are indeed capable of conferring differential gene expression during seed development. This was investigated by transferring AP1-GUS, napin-GUS and cruciferin-GUS chimaeric genes into tobacco and monitoring their expression at various stages throughout seed development, whereas similar experiments with expression of these combinations in rape are in progress.

The 1.4 kb 5' upstream fragment of the ACP05 gene, a 1.1 kb upstream fragment of a rape napin gene and a 2 kb upstream fragment of a rape cruciferin gene were fused to the β-glucuronidase (GUS) reporter gene and transferred into tobacco via Agrobacterium infection. GUS activity was assayed in seed from two stages of development (mid-mature and mature) and in leaf tissue. All three rape promoters were found to regulate GUS expression in a seed-specific manner, but they differed in their mode of temporal regulation during seed development. Thus with AP1-GUS transformed plants, GUS activity was maximal in mid-mature seeds, whilst in plants transformed with the two storage protein promoter constructs, GUS activity was maximal in mature seed (see FIG. 12).

The maximal level of GUS expression obtained in tobacco seeds with both the ACP and cruciferin promoters was similar to that obtained with the powerful constitutive cauliflower mosaic virus 35S promoter (average of 10 plants/construct), and approximately 3x that obtained with the napin promoter.

A second study was carried out to determine more precisely the nature of the temporal differences conferred on GUS expression during seed development by a lipid biosynthetic gene promoter (AP1) and a storage protein gene promoter (cruciferin). Seed from the highest expressing AP1GUS and CRUGUS plants of the first study were used to propagate new plants. Flowers were tagged on opening and 7–20 days after flowering seed pods were collected and the GUS activity of seed extracts determined. In plants transformed with the ACP promoter-GUS fusion, activity peaked at 11–12 DAF corresponding to the maximum rate of lipid synthesis in the seed. In plants transformed with the cruciferin promoter-GUS fusion, activity peaked at 16–19 DAF, which corresponded to the stage in seed development when protein content was rapidly increasing but the rate of lipid synthesis was decreasing (see FIG. 14).

The results of these findings have important implications for a programme aimed at modifying rapeseed oil composition via genetic engineering. In order to be successful a transferred gene, encoding a protein that may perturb fatty acid biosynthesis, should be expressed coincidentally with the lipid synthetic phase of seed development. The present results clearly demonstrate that in order to achieve that objective, the expression of the transferred gene would have to be controlled by a seed lipid biosynthetic gene promoter, e.g. of an ACP gene. Fusion of the gene to a seed storage protein gene promoter, e.g. of a napin gene, would result in maximal expression of the transferred gene after the most active phase of lipid synthesis and would, therefore, not likely result in a significant perturbation of the fatty acid profile.

Thus the present invention provides a new seed lipid biosynthetic gene promoter, and its use in expressing a gene at such stage in the seed development that the protein or polypeptide formed can influence the biosynthetic formation of fatty acids and lipidic esters thereof. Although the invention is illustrated on the basis of a nature-identical plant promoter isolated from a particular Brassica napus species, it will be clear to a skilled person that other nature-identical seed-specific promoters that are also capable of expressing genes in concert with the fatty acid or lipid biosynthesis can be isolated using the teachings of the present specification. The expression "in concert with" used in this specification means that the gene is expressed at such place and at such time that the protein resulting from the expression can play a role in the fatty acid or lipid biosynthesis in the plant cell. Specifically said promoter has the ability to express a gene placed under control of said promoter at a stage before or during fatty acid or lipid biosynthesis.

Moreover, by using known techniques for DNA modification, other DNA sequences can be prepared that can be tested for their ability to promote gene expression in a seed-specific and temporal fashion.

Thus in a broader sense the expression "promoter that is capable of acting as a seed-specific plant promoter" covers both nature-identical promoters and modifications thereof that are also active as seed-specific plant promoters, as well as otherwise designed promoters being active as seed-specific plant promoters.

Therefore, the present invention relates to a recombinant DNA construct containing a promoter that is capable of acting as a seed-specific plant promoter, said promoter being also capable of expressing a gene placed under control of said promoter in concert with the fatty acid or lipid biosynthesis in a plant cell.

The expression "recombinant DNA construct" is used in this specification to exclude similar DNA sequences in their natural environment. It indicates that human intervention is used to prepare the construct, which can then be incorporated into plants and stably inherited in their progeny. For example, the nature-identical promoter can be combined with a structural gene different from the gene it controls in nature. Or it can be combined with an enhancer to increase the level of transcription of its natural gene. The level of production of the protein encoded by its natural structural gene can be reduced by combining the promoter with anti-sense DNA, or by combining with a truncated structural gene. These methods are described in the prior art. Of course, one can also apply these methods to a heterologous gene.

Or it can be combined with antisense DNA to reduce the level of production of the protein encoded by its natural structural gene.

More specifically the promoter in said DNA construct comprises at least the 291 bp polynucleotide of clone ACP05 given above. This DNA sequence was determined from the 1 kb PstI-BglII 5' upstream fragment of the rape ACP05 gene given in FIG. 1. The larger 1.4 kb BamHI-BglII 5' upstream fragment of the genomic rape ACP05 gene given in FIG. 1, called the AP1 promoter, was taken up in plasmid pAP1GUS present in *E. coli* JM101-/pAP1GUS (NCIMB 40396).

Another embodiment of the invention is the use of a DNA construct containing a seed-specific promoter according to the invention for transforming plant cells, preferably for modifying the seed-specific biosynthesis of fatty acids. Preferably the plant cells are subsequently grown to whole plants in which the modified biosynthesis of fatty acids occurs specifically in the seeds. A practical embodiment of such use is a process of transforming plant cells, in which a DNA construct containing a seed-specific promoter according to the invention is introduced into a transformable plant cell in such a way, that after growing the resulting transformed plant cell to whole plants the structural gene forming part of said gene controlled by the introduced seed-specific and temporally regulating plant promoter is expressed in concert with the fatty acid or lipid biosynthesis in the seeds of the plants, thereby producing the protein corresponding to said structural gene. In one preferred way of carrying out such process said structural gene encodes a protein required for the seed-specific biosynthesis of fatty acids or the corresponding lipids.

Such process can result in a method for modifying the formation of vegetable seed oils, which method comprises growing a plant cell via plantlet to a plant bearing seed and harvesting the resulting seed containing a vegetable oil with modified composition, whereby the cells of said plant cell or plant or seed comprise a DNA construct according to the invention, in particular, if said DNA construct comprises a gene encoding a protein active in the biosynthetic pathway for fatty acid production or lipid formation, and the protein or proteins introduced in this way can modify the biosynthetic pathway.

If a promoter essentially consisting of a seed-specific ACP promoter, preferably one originating from *Brassica napus* and a structural gene encoding ACP is used, the latter should differ from the wild-type gene.

This embodiment may result in seeds comprising a DNA construct according to the invention, but if said DNA construct contains a seed-specific plant promoter homologous to the seed, said DNA construct should be present in the genome of said seed at a site other than the natural site for said promoter.

Another embodiment of the invention relates to a seed, preferably of the Brassica family, wherein said DNA construct also contains a DNA sequence of interest encoding an exogenous protein, whereby the DNA sequence of interest is under control of the seed-specific plant promoter. However, for practical purpose the exogenous protein should be present in addition to the DNA construct. This latter embodiment is thus mainly directed to a process for producing a desired protein in plant cells, preferably seed cells, which comprises expressing a structural gene encoding said protein, said plant cells containing a recombinant DNA construct according to the invention comprising said structural gene, the production of said protein. For some applications, e.g. animal feedstuff or for human consumption, it is sufficient if the seeds contain the desired protein, because the seeds can be used as such. For other applications it is desirable that such process is followed by isolation of said protein from the plant cells.

The invention is illustrated by the following Examples without being limited thereto.

Mostly standard methods were used as described in Maniatis, T., Fritsch, E. F., & Sambrook, J.; Molecular Cloning; Cold Spring Harbor Laboratory Publ. (1982). If modifications were used, they are described below. The following restriction sites are mentioned in this specification:

| BamHI  | G↓GATCC | KpnI  | GGTAC↓G |
| BglII  | A↓GATCT | PstI  | CTGCA↓G |
| EcoRI  | G↓AATTC | SalI  | G↓TCGAC |
| HaeIII | GG↓CC   | Sau3A | ↓GATC   |
| HindIII| A↓AGCTT | SstI  | GAGCT↓C |

EXAMPLE 1

Isolation of *B. napus* ACP promoter a) Isolation of ACP genomic clones

Nuclear DNA was isolated from leaves of field grown *B. napus* plants. Leaves were homogenised in 0.6M sucrose, 50 mM Tris-HCl pH 8.0, 10 mM $MgCl_2$, 10 mM β-mercaptoethanol, the nuclei pelleted, washed twice in the same homogenisation buffer also containing 1.2% Triton X-100 and lysed in 50 mM Tris-HCl pH 8.0, 20 mM EDTA, and 1% Sarkosyl. DNA was purified by phenol extraction/CsCl centrifugation, partially digested with Sau3A and fractionated by sucrose density gradient centrifugation. 15–20 kb DNA was ligated to BamHI-digested lambda EMBL 4 arms previously purified by electroelution from agarose. The ligation mixture was packaged using Gigapack Plus extracts (ex Stratagene) and propagated in *E. coli* K803. The resultant library was screened with a $^{32}$P-labelled RNA probe derived from ACP cDNA clone 29CO8 (R. Safford et al. (1988) supra), cloned into a SP6 vector (ex Amersham), and positive plaques obtained. One of these, designated ACP05, was purified, the DNA was isolated and subcloned into pTZ18R (ex United States Biochemical Corp.) and characterised by restriction mapping and DNA sequencing.

b) Structural analysis of ACP05

ACP05 DNA was digested with a range of restriction enzymes and the cleavage sites mapped (FIG. 1). Restricted DNA was Southern blotted to identify DNA fragments with homology to the ACP RNA probe described above. A 1.15 kb HindIII fragment, a 5 kb BamHI fragment and a 1 kb SalI fragment were found to hybridize (see FIG. 1). Overlapping restriction fragments were sub-cloned into M13 vectors and DNA sequenced using a modified bacteriophage T7 DNA polymerase (ex United States Biochemical Corp.). Universal and synthetic oligonucleotide primers were used to obtain a total of about 2233 bp of sequence (FIG. 3). Using dot matrix analysis homology was found between the DNA sequences of ACP05 and rape embryo cDNA clone 29CO8, see (FIG. 2), thus confirming that the cloned genomic fragment encoded an ACP gene. Alignment of the nucleotide sequences of genomic clone ACP05 and cDNA clone 29CO8 identified 3 intervening sequences (introns) within the ACP gene corresponding to nucleotides 1048–1317, 1426–1501, and 1625–1726 of the genomic sequence given in FIG. 3. Complete homology (100%) was found between the exons and the seed expressed cDNA sequence, providing evidence that the ACP05 gene is expressed in the seed.

To determine the transcription start site of ACP05 and hence also to define the start of the upstream regulatory sequences of the gene, RNase protection studies were carried out (see J. de Silva et al. (1990) supra). A 1 kb PstI-SalI fragment of genomic clone ACP05, spanning the predicted transcription start site of the gene, was ligated into the SP65 transcription vector (ex Amersham) and used as a template to produce full length $^{32}$P-labelled antisense ACP RNA. The antisense probe (about 200,000 dpm) was hybridised to *B.*

*napus* embryo poly A⁺ RNA, isolated according to (R. Safford et al. (1988) supra), and to an RNA transcript of ACP cDNA clone 29CO8 in 50% formamide, 40 mM PIPES pH 6.4, 0.4M NaCl, 1 mM EDTA at 45° C. overnight followed by treatment with RNase A (40 mg/l) and RNase TI (2 mg/1) for 30 minutes at 30° C. (dpm=desintegrations per minute, PIPES =piperazine-N,N'-bis[2-ethanesulfonic acid] or 1,4-piperazine diethanesulfonic acid ex Sigma). RNase activity was destroyed by treatment with proteinase K (125 mg/l) and SDS (0.5%) for 30 minutes at 37° C. Protected RNA was recovered by phenol/chloroform extraction and ethanol precipitation and analysed on a 6% acrylamide/urea sequencing gel. The major fragment protected by embryo poly A⁺RNA was found to be 12 bases longer than the major fragment protected by the cDNA derived transcript.

This result therefore identifies the start of transcription of ACP05 as 12 bases upstream from the 5' end of ACP cDNA 29CO8, at the first adenine within the sequence GGCATCA, and defines the length of the 5' non-coding sequence as 69 nucleotides (FIG. 3).

c) Functional analysis of ACP05 promoter

To evaluate the ability of the 5' upstream region (promoter) of ACP05 to confer seed specific and temporal regulation of gene expression in plants, a transcriptional fusion was made between a 1.4 kb 5' upstream fragment of ACP05 and the reporter gene β-glucuronidase (GUS). The chimaeric gene (AP1GUS) was transferred into tobacco and expression of GUS activity was monitored in leaf and seed tissue of the resultant transgenic plants.

c.1) Construction of pAP1GUS

A 2.5 kb BamHI-SstI restriction fragment of genomic clone ACP05, containing approximately 1 kb of the transcriptional unit of the gene together with 1.5 kb of the 5' upstream region of the gene, was cloned into pTZ18R (see Example 1.a) to form pTZ5BS. This recombinant plasmid was linearised by digestion with BamHI and partially digested with BglII to produce restriction fragments of 4.9, 3.8, 3.5, 1.4, 1.1 and 0.3 kb in length. The 1.4 kb BamHI-BglII fragment, containing the promoter region of the gene, was recovered and ligated into BamHI-linearised, phosphotased pTAK vector DNA (FIG. 4) to form pAP1GUS (PTAK is a binary plant transformation vector ex Clontech Labs. Inc., containing a GUS marker gene between the T-DNA border sequences which define the region of DNA capable of transfer to the plant chromosome following agroinfection of damaged plant tissue; in addition to the GUS gene, the T-DNA contains the bacterial neomycin phosphotransferase, NPTII, gene which confers resistance to the antibiotic kanamycin, thus allowing for selection of transformed plant cells). The mix containing PAP1GUS was used to transform commercially available *E. coli* JM101 and recombinant clones were screened to confirm insertion of a single promoter fragment in the correct orientation.

c.2) Transformation of Agrobacterium with pAP1GUS

The recombinant pAP1GUS plasmid was mobilised, in a triparate mating, from *E. coli* JM101 to *Agrobacterium tumefaciens* ACH5/pLBA4404 (see A. Hoekema et al.; Nature 303 (1983) 179–181) using commercially available *E. coli* HB101 carrying the helper plasmid pRK2013 (Holsters et al.; Mol. Gen. Genet. 163 (1978) 181–187). An overnight culture of the recipient Agrobacterium strain and exponential cultures of the donor and helper *E. coli* strains were grown. Of each culture 2 ml was centrifuged and the cells resuspended in 1 ml 10 mM MgSO₄. Equal amounts of the 3 cell suspensions were mixed, spread on L-agar plates and incubated overnight at 28° C. Resultant bacterial lawn was suspended in 10 mM MgSO₄ and plated onto L-agar containing 50 mg/l rifampicin+50 mg/l kanamycin. Rifampicin-resistant, kanamycin-resistant colonies were selected, plasmid DNA isolated, transformed back into *E. coli* and characterised by restriction analysis to verify the presence of intact copies of pAP1GUS.

c.3) Transformation and regeneration of tobacco

This was performed essentially as described by Horsch et al.; Science 227 (1985) 1229–1231. Leaf discs of *Nicotiana tibacum* (var.SR1) with a diameter of 0.5 cm were incubated for 10 min with an overnight culture of *A. tumefaciens* ACH5 containing pLBA4404/pAP1GUS. After blotting dry, discs were placed on *Nicotiana plumbaginifolia* feeder plates, prepared by plating 2 ml of haploid *N. plumbaginifolia* suspension culture (Barfield et al.; Plant Cell Reports 4 (1985) 104–107) onto petri dishes containing 20 ml of shoot-inducing medium [0.9% agar, MS salts, 3% sucrose, 0.02 mg/l indole acetic acid (IAA), 1 mg/ml benzylaminopurine (BAP)]. MS-media were described by Murishige, T. & Skoog, F. in Physiol. Plant 15 (1962) 473–497.

After 3 days in culture, discs were transferred to shoot-inducing medium containing 500 mg/l cefotaxime and 100 mg/l kanamycin. Shoots regenerating on selective media were excised and placed on minus hormone media (MS salts, 3% sucrose, 0.9% agar) containing 500 mg/l cefotaxime. Once roots had become established, shoots were again excised and placed on minus-hormone medium containing 100 mg/l kanamycin. Plants that rooted on selective media were transferred to soil and grown at 25° C. under a 16 hour photoperiod (=AP1GUS plants).

c.4) Southern analysis of transformed plants

DNA was isolated from leaves of regenerated AP1GUS plants (Dellaporta; Plant Mol. Biol. Reporter 1 (1983) 19–21), restricted with PstI and EcoRI, transferred to nitrocellulose and hybridised to a $^{32}$P-labelled ACP RNA probe. A 3.0 kb PstI-EcoRI hybridising fragment was indicative of integration of an intact ACP promoter-GUS cassette into the plant genome, and 15 plants whose DNA digests showed this fragment were chosen for further analysis. Scanning laser densitometry of autoradiographs showed the number of copies of the AP1GUS gene in transformed plants to vary from 1 to 4.

c.5) Analysis of transformed plants for GUS enzyme activity

GUS activity was monitored in leaf tissue and in seeds at various stages of development. Under the particular growth conditions used the rate of development of individual seed pods on a single tobacco plant was found to be variable, with the earliest pods frequently developing the fastest. As such it was not possible to use DAF to accurately determine the developmental stage of a seed. For this reason, seeds were staged using morphological characteristics. Five stages of seed development were identified on the basis of seed size and pigmentation:

1. 0.4–0.5 mm long and no pigment (white)
2. 0.5–0.6 mm long and light brown
3. 0.6–0.8 mm long and pigmented with a hard seed coat
4. 0.6–0.8 mm long and highly pigmented (brown)
5. Desiccated (which is called mature seed)

The nature of the relationship between DAF and the various stages of seed development are shown in FIG. 5.

15 AP1GUS transformed plants were analysed for GUS activity along with 4 control plants which were transformed with pcTAK, a construct containing the GUS gene linked to the constitutive plant promoter, cauliflower mosaic virus (CaMV) 35S—this construct was kindly provided by Richard Jefferson, Plant Breeding Institute, Cambridge.

Extracts from leaf and seed stages 1, 2 and 3 of the APIGUS and pcTAK transformed plants were assayed for GUS activity by incubation with methyl umbelliferyl glucuronide (MUG) and measurement of the fluorescence of released methyl umbelliferone (MU). Plant extracts were prepared by grinding tissue on ice in GUS extraction buffer [50 mM sodium phosphate pH 7.5, 0.1% Triton X-100, 1 mM EDTA, 10 mM dithiothreitol (DTT), 1 mM phenylmethylsulphonyl fluoride (PMSF)] in the presence of acid washed sand. Insoluble material was removed by centrifugation for 5 minutes in a bench top centrifuge. Of the soluble extract 0.05 ml was incubated with 1 ml of assay buffer [=GUS extraction buffer containing 1 mM MUG] at 37° C. and 0.25 ml aliquots were removed at 0, 5, 15 and 30 minutes into 0.75 ml 0.2M $Na_2CO_3$. MU fluorescence was measured on a Baird Nova 1 spectrofluorimeter set at excitation wavelength 365 nm and emission wavelength 455 nm.

Consistent patterns of GUS activity were obtained in individual transformed plants in terms of tissue specificity and developmental regulation, although the absolute levels of expression varied considerably from plant to plant (FIG. 6). The variable levels of gene expression obtained within the transgenic population is a common phenomenon and is thought to be due to position effects resulting from random integration of the transferred DNA (Jones et al.; EMBO J. 4 (1985) 2411–2418). There was no correlation between level of GUS expression and copy number of inserted genes.

In pAP1GUS transformed plants, the level of GUS activity (pmol MU/minute/mg fresh wt.) in leaf tissue was very low (average value=7.2), compared to seed tissue where it was found to increase through development from an average of 68.7 in stage 1 to 301 in stage 3. In contrast, in plants transformed with pcTAK, the level of GUS expression was higher in leaf (average value=237) than in seed tissue where the average value dropped from 188 at stage 1 to 56 at stage 3 (see FIG. 6).

The relative level of GUS activity in seed tissue compared to leaf was calculated for each of the seed stages of the AP1GUS and cTAK transformed plants. This provides data on the tissue specificity/developmental regulation of expression that is independent of plant to plant differences in absolute levels of GUS activity. The average values obtained from 13 AP1GUS plants and 4 cTAK plants are presented in the form of a histogram (FIG. 7). In AP1GUS transformed plants the level of GUS activity increases during seed development to reach a maximum value that is, on average, 100-fold higher than that observed in leaf tissue. In contrast, in cTAK plants, the level of GUS activity in all 3 seeds stages of seed development is similar to that found in leaf tissue and thus the average seed/leaf values approximate to 1. This data therefore demonstrates that the isolated AP1 promoter functions to control gene expression in a seed specific, developmentally regulated fashion.

Furthermore, comparison of GUS expression in stage 3 seeds of AP1GUS and cTAK transformed plants shows a higher average level of activity in the APLGUS plants. Since the CaMV 35S promoter present in the cTAK construct is widely acknowledged as a powerful constitutive plant promoter, it follows that the AP1 promoter that has been isolated is itself a powerful promoter for expressing genes in this particular tissue.

EXAMPLE 2

Deletion analysis of ACP promoter fragment

The 1.4 kb ACP promoter fragment described in Example 1 was subjected to deletion analysis to define more precisely the location of sequences which are able to confer tissue specific, developmental regulation of gene expression.

Chimaeric gene constructs containing 1.4 kb (pAP1GUS), 0.93 kb (pAP3GUS) and 0.29 kb (pAP2GUS) respectively of the 5' upstream region of the acyl carrier protein gene ACP05 fused to the β-glucuronidase (GUS) reporter gene were transferred into tobacco and the resultant transformed plants assayed for expression of GUS activity.

a) Construction of PAP1GUS

See Example 1.

b) Construction of pAP2GUS (see FIG. 8)

pTZ5BS DNA (see Example 1, item c.1) was digested to completion with BglII, producing restriction fragments of 3.5, 1.1 and 0.3 kb in length. The 0.3 kb fragment was ligated to BamHI linearised pTAK and the mix used to transform E. coli RRI.

Recombinant clones were screened by digestion with PstI+SstI and HindIII to confirm insertion of a single promoter fragment in the correct orientation. The resultant plasmid AP2GUS contains 0.29 kb of the ACP promoter linked to the GUS gene.

c) Construction of AP3GUS (see FIG. 9)

pTZ5BS DNA was digested to completion with PstI, self-ligated and the mix used to transform E. coli RRI. Recombinant clones were screened for recircularised large PstI fragment by digestion with HindIII yielding a plasmid indicated with pTZ5PS. DNA of this latter plasmid was digested with HindIII, the 1 kb promoter fragment recovered, ligated into HindIII digested AP2GUS DNA and transformed into E. coli RRI. Recombinant clones were screened by digestion with PstI+BglII for the presence of the 1 kb promoter fragment instead of the 0.29 kb AP2 promoter fragment. The resultant plasmid (pAP3GUS) contains the GUS gene linked to and under control of the first 924 bp of the ACP promoter immediately upstream of the transcriptional start site of the structural ACP gene.

d) Transformation of Agrobacterium The vectors pAP1GUS, pAP2GUS, pAP3GUS were transferred into A. tumefaciens ACH5/pLBA4404, along with control vectors pcTAK and pTAK (a promoterless GUS gene construct) using a direct DNA uptake protocol (An et al.; Binary vectors; In: Plant Molecular Biology Manual (edited by Galvin and Schilperoort) A3 (1988) 1–19). Transformed colonies were selected, plasmid DNA isolated, transformed back into E. coli and resultant plasmids subjected to restriction analysis to confirm the presence of intact copies of the respective genes.

e) Tobacco transformation

As described in Example 1.

f) Southern analysis of transformed plants

Regenerated plants were confirmed to contain inserted copies of intact chimaeric genes via Southern analysis as described in Example 1.

g) Analysis of transgenic plants for GUS activity Extracts from leaf and seed stages 3 and 5 of transgenic plants were assayed for GUS activity (10 plants per construct group). In this experiment GUS activity was expressed as a function of DNA, which represents a more constant cell parameter than either fresh weight or protein concentration, both of which increase dramatically during the cell expansion phase of embryo development. During initial DNA estimation of leaf extracts it was found that Triton X-100, present in the GUS extraction buffer (see Example 1), interfered with measurement of DNA concentration using the Hoechst method. SDS was able to replace Triton X-100 without interference and was used in subsequent extractions.

As described in Example 1, the absolute level of GUS expression (pMol MU/minute/μg DNA) in individual plants was found to vary considerably. However, consistent tissue patterns of GUS expression were obtained in individual plants from each construct group. The mode of GUS expression in plants transformed with the 2 deleted ACP promoter constructs (AP2GUS and AP3GUS) showed no difference to that obtained in plants transformed with the 1.4 kb promoter (AP1GUS). Thus plants transformed with each of the 3 ACP promoter constructs had higher levels of expression in seed than leaf, with maximum activity in stage 3 seeds. By contrast, plants transformed with pcTAK showed similar levels of expression in seed and leaf tissues. FIG. 10 shows the values obtained from averaging the GUS activity of the 10 plants in each construct group. In the 3 groups transformed with the ACP promoter constructs, GUS activity is highest in stage 3 seed>mature seed>leaf (the level of activity in leaf was no higher than the background level obtained in plants transformed with the promoterless PTAK construct), thus demonstrating that both deleted versions of the ACP promoter still contain the elements responsible for tissue specific and developmental regulation. In regard to levels of GUS activity, the 0.29 kb ACP promoter construct (AP2GUS), in fact showed slightly higher average levels of activity than the 1.4 kb promoter, which in turn was higher than the 924 bp AP3 promoter values.

In conclusion, it has been shown that the elements conferring both tissue specific, developmental regulation and also level of expression of gene ACP05 reside within 0.29 kb of the transcription start site of the gene.

EXAMPLE 3

Comparison of ACP, napin and cruciferin promoters from rape

In oil seed rape, synthesis of the various storage products during seed development is differentially regulated. Thus storage lipid is synthesized first, followed by the two storage proteins, napin and cruciferin. It might be that this regulation is mediated by specific groups of seed promoters differentially activating the genes responsible for the synthesis of the various storage products during seed development.

The purpose of the study described in this Example was to determine if the respective rape promoter elements from a lipid biosynthetic gene (ACP) and from 2 storage protein genes, (napin and cruciferin) are indeed capable of conferring differential gene expression during seed development. This was investigated by transferring chimaeric ACP-GUS, napin-GUS and cruciferin-GUS genes into tobacco and monitoring their expression at various stages during seed development.

Construction of chimaeric genes

The construction of pAP1GUS, the transcriptional fusion between the 1.4 kb 5' upstream region of ACP05 and the GUS gene was described in Example 1. Constructs containing rape storage protein promoters fused to the GUS gene, cloned into the plant transformation vector pTAK, were obtained from Dr. A. Ryan at Durham University. The latter are respective transcriptional fusions (FIG. 11) between a 1.1 kb napin 5' upstream fragment and the GUS gene (pNAPGUS) and a 2.0 kb cruciferin 5' upstream fragment and the GUS gene (pCRUGUS).

Vectors were transferred into *A. tumefaciens* ACH5-/ pLBA4404 as described in Example 2 and these were used to transform tobacco, along with pTAK and pcTAK controls, as described in Example 1. Ten plants were regenerated for each construct.

Southern analysis

Regenerated plants were confirmed to contain inserted copies of intact chimaeric genes via Southern analysis as described in Example 1.

Analysis of transgenic plants for GUS activity

Experiment 1

GUS activity was assayed in leaf and seed stages 3 and 5 of the transgenic plants as described in Example 2. Consistent patterns of GUS activity in the tissues examined were obtained for individual plants in each construct group, although absolute values varied (as noted previously in Examples 1 and 2).

In plants transformed with either napin or cruciferin constructs the level of GUS activity in leaves was low (FIG. 12) and maximum activity was observed in stage 5 seed. With napin transformants, GUS activity in stage 3 seeds was, on average, 75% of maximum, whilst with cruciferin transformants only 30% of maximum activity was observed in stage 3 seeds.

With APLGUS transformed plants, maximum GUS activity was observed in stage 3 seeds, and this was, on average, 2.5 fold higher than in stage 5 seed.

These results demonstrate an earlier activation of the ACP promoter during seed development compared to the 2 storage protein gene promoters. To be able to determine the nature of this differential activation more accurately, a second experiment (see below) was carried out employing a detailed seed staging GUS analysis.

Comparison of the average values of GUS activities obtained from each of the construct groups allows a quantitative evaluation of the relative promoter strengths. In AP1GUS transformed plants the maximum level of GUS activity, in stage 3 seed was similar to that obtained in stage 5 seed of pCRUGUS transformed plants (also similar to the maximum level obtained in pcTAK transformed plants in leaf tissue). This value was approximately 3 fold higher than the maximum observed in pNAPGUS transformed plants, in stage 5 seed.

Experiment 2

Seed from the highest GUS expressing transgenic AP1GUS and CRUGUS plants was germinated on kanamycin and the resultant FI plants were used to carry out a detailed analysis of GUS expression during seed development.

In earlier studies (see Example 1), where plants were grown in 5 inch pots and all of the flowers pollinated, a variable rate of pod development was observed and hence morphological characteristics were used to stage seed development. In order to be able to determine more accurately the nature of the observed differential gene activation conferred by the ACP and storage protein gene promoters, an alternative system of flower tagging was utilised, which did enable DAF to be used as a meaningful marker for seed development. Thus, at the start of flowering, tobacco plants were transferred to 7.5 inch diameter compost pots. Each day at a pre-set time, the number of new flowers with anthers open was scored, a single flower was tagged and the remaining flowers removed. Tagging was carried out for 14 days (day 0 to day 13) and on day 20, all 14 pods were harvested, representing 7–20 DAF. Seeds were collected and assayed for protein and lipid content. Protein estimation was carried out by homogenising seeds in 0.1% SDS, 1M NaCl, 50 mM sodium phosphate pH 7.5, 1 mM EDTA, 10 mM dithiothreitol, centrifuging and assaying the supernatant using a protein reagent (ex Bio-Rad). Total fatty acid content was determined by extraction of seeds in chloroform/methanol (2:1) and GLC analysis of fatty acid methyl esters produced by refluxing the extracted lipids with methanol:toluene:conc. sulphuric acid (20:10:1). The data obtained on the synthesis of lipid and protein during seed development is shown in FIG. 13. Fatty acid content is seen to increase sharply between days 9 and 13, whilst the major phase of protein synthesis occurs during days 17 to 20. The sigmoidal patterns of accumulation observed for the 2 storage products shows that, under these established growth conditions, flower tagging can be used as a meaningful developmental marker.

'Tagged' seeds were extracted and analysed for GUS activity as described in Example 1. FIG. 14 shows that in AP1GUS transformed plants, GUS activity (average of 2 plants) commenced at 9 DAF, reached 50% of maximum at 10 DAF and peaked at 11–12 DAF, corresponding to the most active phase of lipid synthesis. By 14 DAF, activity had fallen to 20% of maximum and it remained at this level until 20 DAF (stage 5).

In CRUGUS transformed plants GUS activity was 1.3% of maximum at 10 DAF and only 7% of maximum at 11 DAF, the phase of most active lipid synthesis. By 15 DAF 50% of maximum activity was reached and activity peaked between 16 and 19 DAF, corresponding to the most active phase of protein synthesis.

Superimposition of GUS activities on fatty acid and protein accumulation during tobacco seed development (FIG. 15) shows GUS expression driven by the ACP promoter to be maximum coincident with the most active phase of lipid biosynthesis, whilst cruciferin promoter driven GUS expression to peak several days later in concert with the major phase of storage protein synthesis.

These findings are of crucial importance to any programme aimed at modifying storage lipid composition by genetic engineering. In order to perturb the process of lipid biosynthesis, the transferred gene must be under the control of a seed lipid biosynthetic promoter. Linkage of the transferred gene to a storage protein gene promoter would lead to expression of the gene after the bulk of the storage lipid had been synthesized within the seed.

EXAMPLE 4

AP1-controlled MCH production in rape This example demonstrates the functionality of the AP1 promoter in the homologous plant i.e. oil seed rape. The AP1 promoter is shown to temporally regulate the expression of a foreign gene during seed development in oil seed rape. The foreign gene used encodes the medium chain s-acyl fatty acid synthetase thioester hydrolase (MCH) from rat. MCH is an enzyme which is induced in the rat mammary gland during lactation, whereupon it causes premature chain termination of fatty acid synthesis resulting in the synthesis of medium chain fatty acids for milk production (Libertini and Smith, J. Biol. Chem. 253, (1978) 1393–1401).

cDNA encoding rat MCH has been isolated and sequenced (R. Safford et al., Biochem. 26 (1987) 1358–1364). In order to target the MCH gene product to the correct intracellular site of fatty acid synthesis within the cotyledon cells, namely the plastid organelle, it was necessary to link the MCH cDNA to a plastid targeting sequence. This sequence was isolated from the rape ACP cDNA (R. Safford et al. (1988) supra). The resultant ACPMCH chimaeric gene was fused to the rape AP1 promoter and the final construct, called pAP1A2M, was transferred, via Agrobacterium infection, into oil seed rape. Historically, pAP1A2M was constructed via a very circuitous route, being the final product of a number of exploratory constructs. Since all the cone component parts of the construct have either been described already in this patent or have been published in the literature, we will, for simplicity, only provide a description of the final construct plus the DNA sequence (see FIG. 16 and the legends to FIG. 16).

The construct comprises the following elements i) ACP promoter

The 1.4 kb BamH1-BglII sequence from clone ACP05 (see example 1: Construction of pAP1GUS) which comprises a sequenced 975 bp PstI-BglII fragment (polynucleotide 7–981 of FIG. 3) of the non-coding part of the gene) plus a further 0.4 kb BamH1-PstI 5' fragment (not sequenced).

ii) ACP transit sequence

A 183 bp Sau3A-HaeIII fragment of ACP genomic clone 05E01 (R. Safford et al. (1988) supra). A BglII linker was attached to the 3' end of the fragment to permit fusion with the MCH structural gene.

iii) MCH structural gene

A fragment representing nucleotides 320–1179 of MCH cDNA clone 43H09 (from the GAG codon immediately downstream of the ATG initiation codon to 71 nucleotides downstream of the translation stop codon), whereby the last two nucleotides AG were enlarged to a BglII linker to facilitate cloning into the plant vector.

In order to preserve the natural cleavage site (C↓A) of the ACP molecule, the junction between the ACP transit sequence and the MCH structural gene was modified by site directed mutagenesis. This involved deletion of a 9 base sequence corresponding to the BglII linker and the ATG initiation codon of MCH. Thus the final pAP1A2M construct encoded a fusion protein consisting of the ACP transit sequence plus the first two amino acids of the mature ACP protein (Ala-Ala) followed by the MCH protein lacking the initiating ATG.

b) Transformation of Agrobacterium tumefaciens A binary vector was constructed by transferring pAP1A2M into *A. tumefaciens* pGV3850 (Zambryski et al., EMBO 2 (1983) 2143–2150) using a direct DNA uptake procedure (An et al. (1988) supra). From the resultant Agrobacterium colonies, DNA was extracted and transformed into *E. coli*, from which it was re-isolated enabling correct gene insertion to be verified.

c) Transformation of *Brassica napus* cv. Westar Stem segments were cut and transformed with *A. tumefaciens* containing the binary vector pGV3850:pAP1A2M. The procedure used was that of Fry et al., Plant Cell Reports 6 (1987) 321–325 with the following modifications:

i. Kanamycin selection was at 20 µg/ml and was delayed until 2 weeks after infection, ii. Carbenicillin was replaced by cefotaxime: 500 µg/ml, iii. Arginine was omitted from the regeneration media, iv. 0.8% agar was replaced by 1% agarose, v. a 2–3 day pretreatment of the stem segments on standard shooting media was carried out prior to infection, and vi. a *N. plumbaginifolia* cell line (Barfield et al. (1985) supra) was used as feeder layer.

Shoots staying green on selective media after 2 transfers were tested for the presence of nopaline (Otten and Schilperoort, B. B. A. 527 (1978) 497–500). Positive shoots were transferred to soil, potted on into 5" pots and transferred to growth rooms operating a 16 hour day (22° C.) and 8 hour night (18° C.) cycle.

d) Analysis of transformed plant tissue

DNA was extracted from leaf tissue, restricted and digests subject to Southern blot analysis, using a KpnI-BglII MCH fragment, to confirm presence of inserted MCH genes.

Seeds were harvested from Southern positive plants at 5 specified developmental stages and analysed for expression of MCH protein using Western blotting. The 5 stages and their relationship to DAF is as follows:

| Stage 1 | <15 DAF | Stage 4 | 25–30 DAF |
| Stage 2 | 15–20 DAF | Stage 5 | 30–35 DAF |
| Stage 3 | 20–25 DAF | | |

Seeds were homogenised in Laemmli sample buffer (Laemmli, Nature 227 (1970) 680–685) (1:1 v/v) using sand as an abrasive. Extracts were boiled for 5 min, microfuged and supernatants removed for analysis. 10 mg equivalent fresh weight of extracts were electrophoresed on 10% SDS-PAGE, blotted onto nitrocellulose and blots reacted with rat-a-MCH antibodies is described in R. Safford et al. (1987) supra.

In the resultant autoradiograph (FIG. 17) the seed extracts show a single cross-reactive band which co-migrates with purified MCH protein. This indicates that the ACP transit sequence of the chimaeric ACP-MCH protein has been processed, presumably upon import of MCH into plastids. The autoradiograph shows MCH expression to be regulated in a temporal fashion during rape seed development. MCH expression is barely detectable in stages 1 and 2, but a dramatic increase is observed during stage 3, just prior to the onset of storage lipid deposition in oil seed rape (see FIG. 18). This result therefore demonstrates that the AP1 promoter functions to express genes specifically in concert with the storage lipid synthetic phase of seed development in oil seed rape.

A culture of E. coli JM101/pAP1GUS was deposited under the Budapest Treaty on 22 Mar. 1991 at the National Collection of Industrial and Marine Bacteria (Aberdeen) and obtained deposit number NCIMB 40396.

In agreement with Rule 28 (4) EPC the availability of a sample to a third person shall be effected only by the issue of a sample to an nominated expert.

Restriction map of ACP05 genomic clone, obtained by digesting ACP05 DNA with restriction enzymes BamHI, PstI, BglII, HindIII, SalI and SstI and mapping of the restriction sites.

FIG. 2

Dot matrix analysis of homology between ACP05 (x axis) and ACP CDNA 29CO8 (y axis) using DNA Star Dotplot software. Blocks of 10 nucleotide sequences are compared and regions sharing 100% homology identified by a dot.

FIG. 3 (1/3–3/3)

Figure 1:
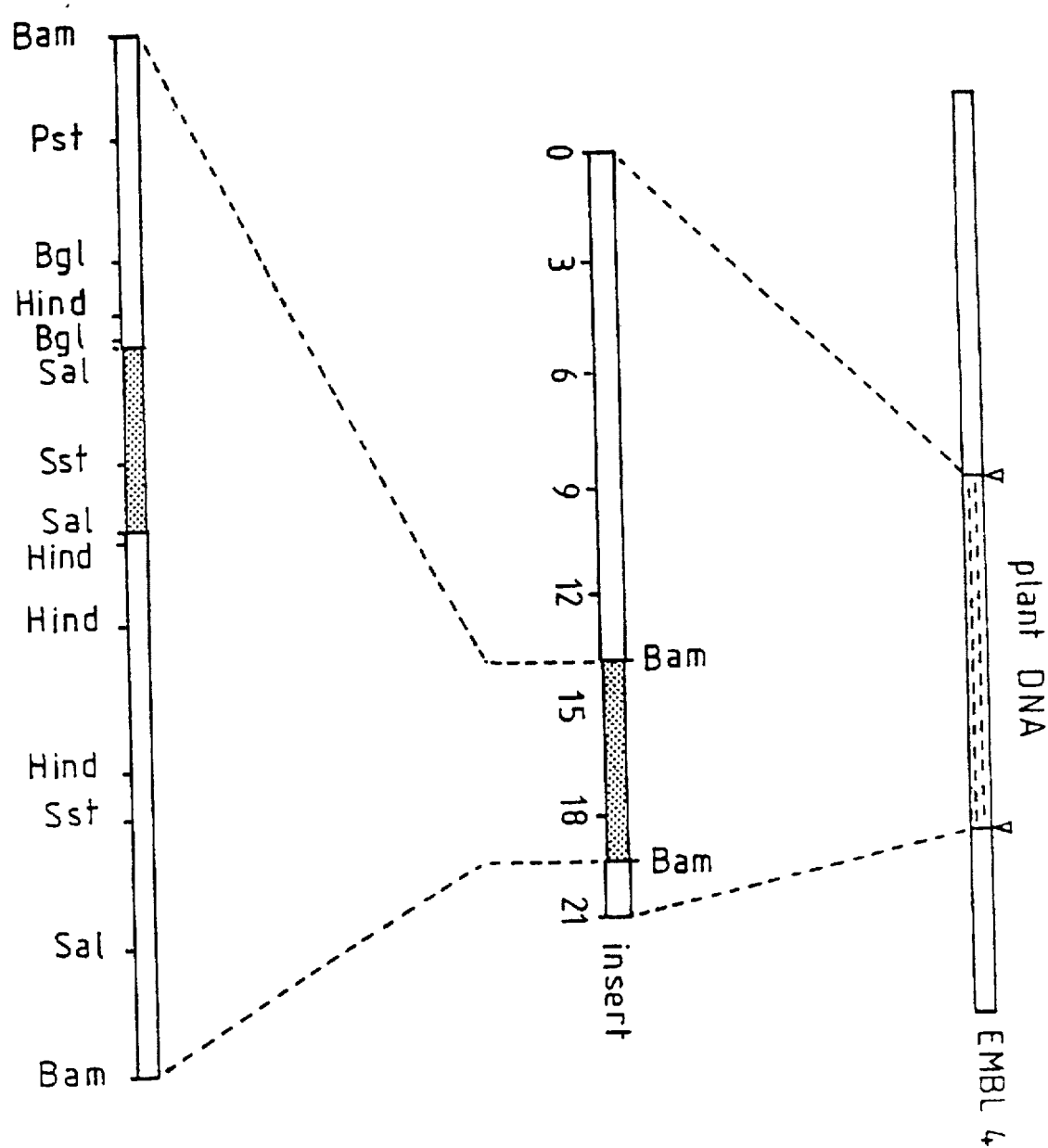
FIG. 1
Figure 2:
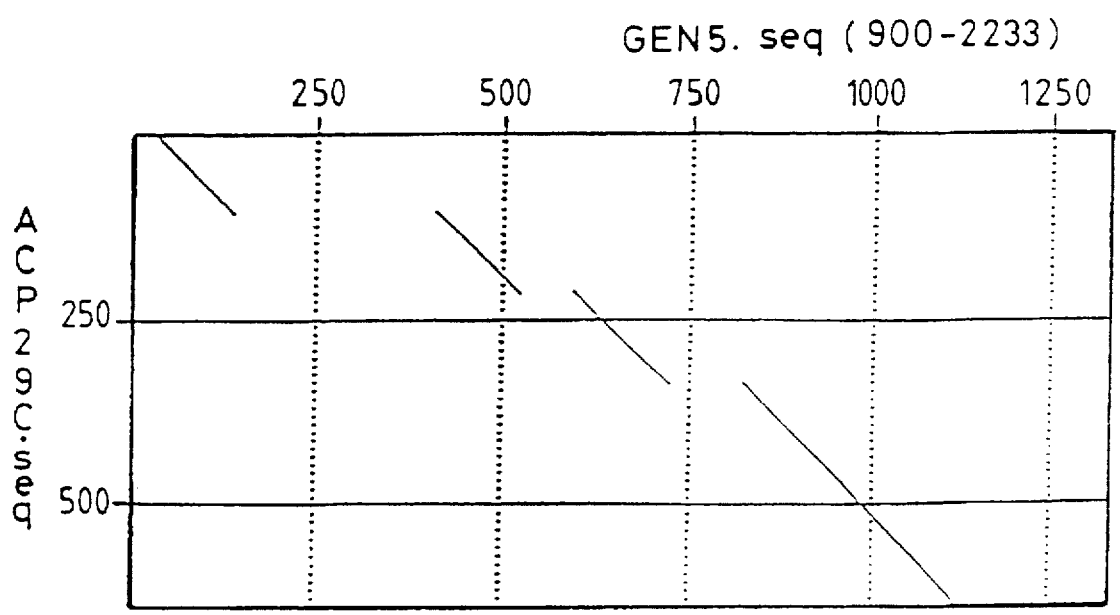
Figure 4:
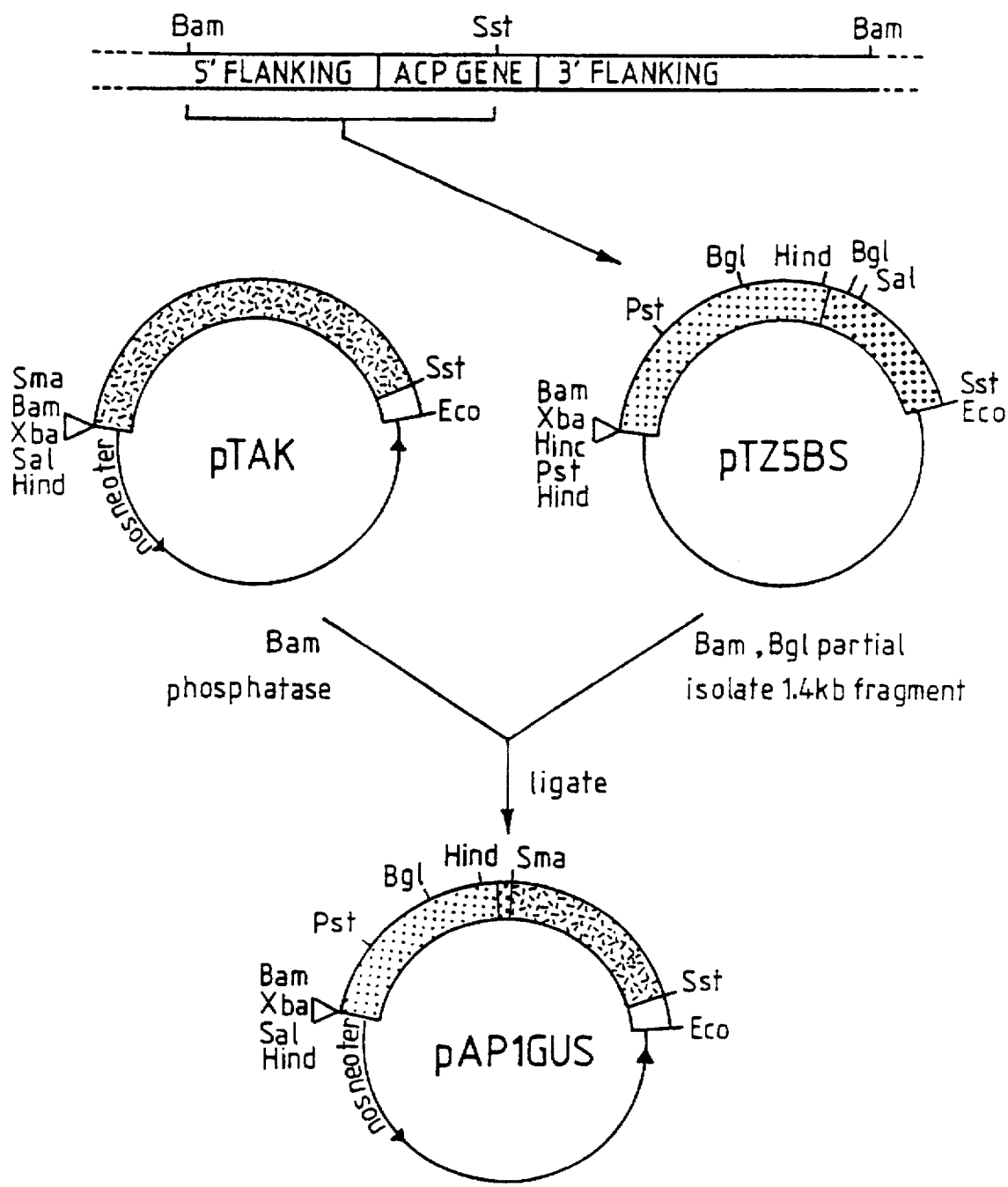
Figure 5:
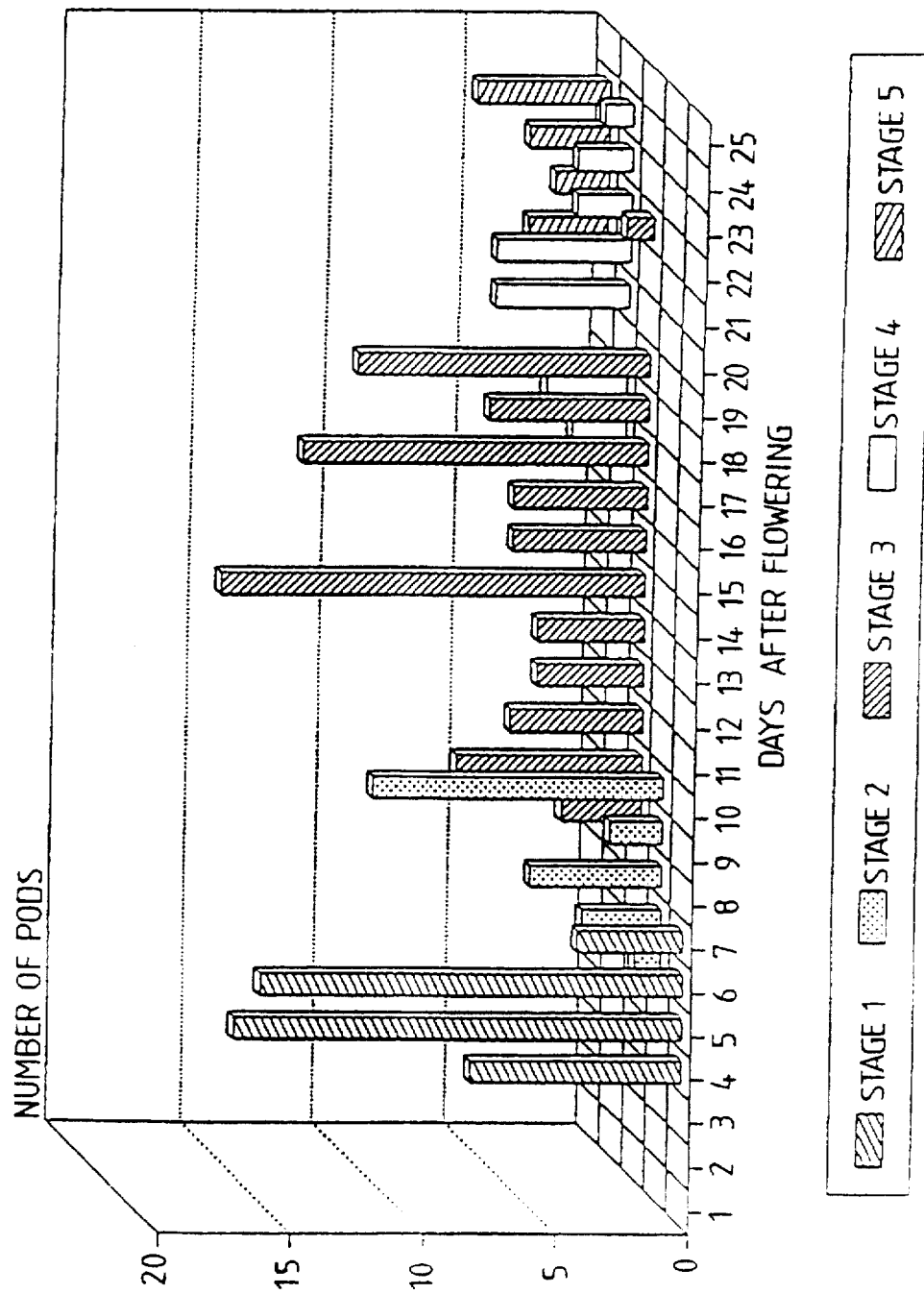
Figure 7:
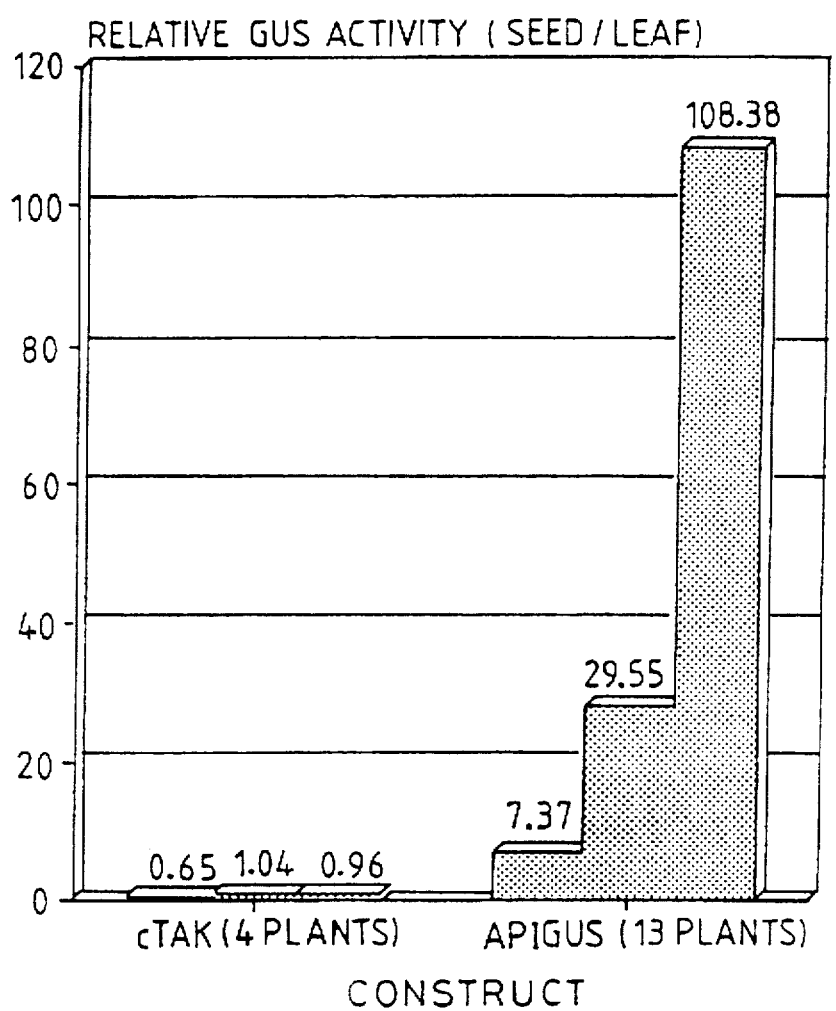
Figure 8:
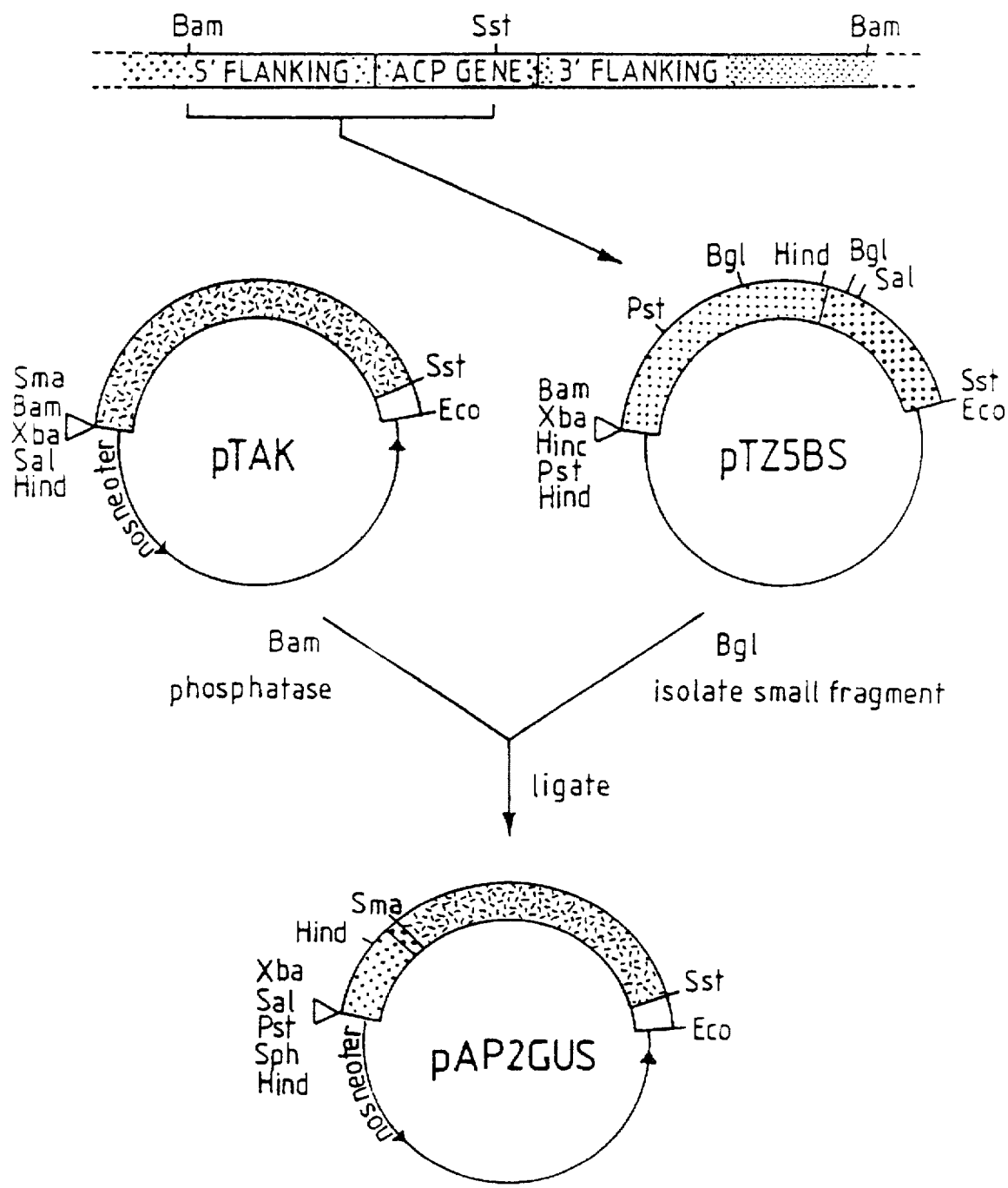
Figure 9:
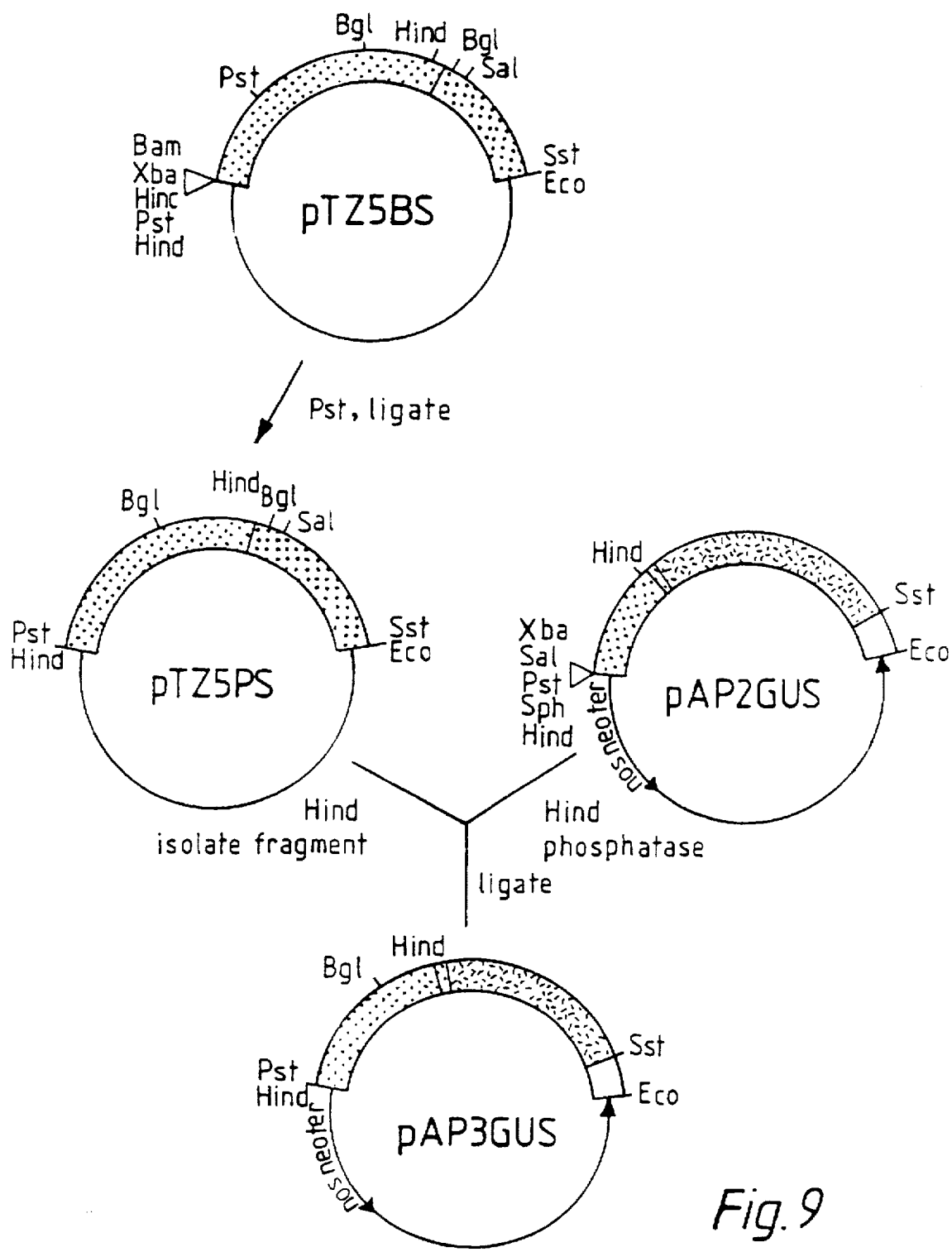
Figure 10:
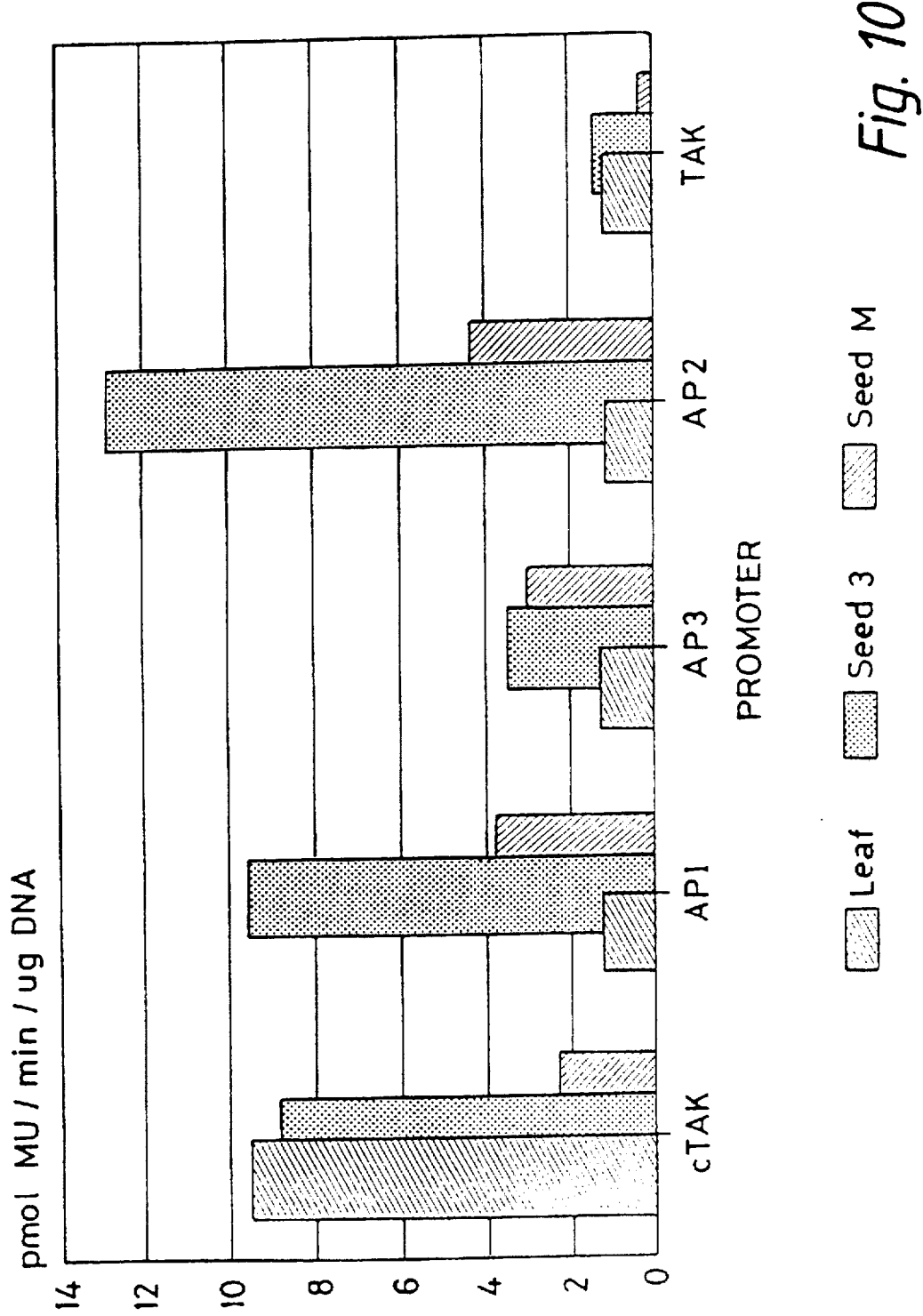
Figure 11:
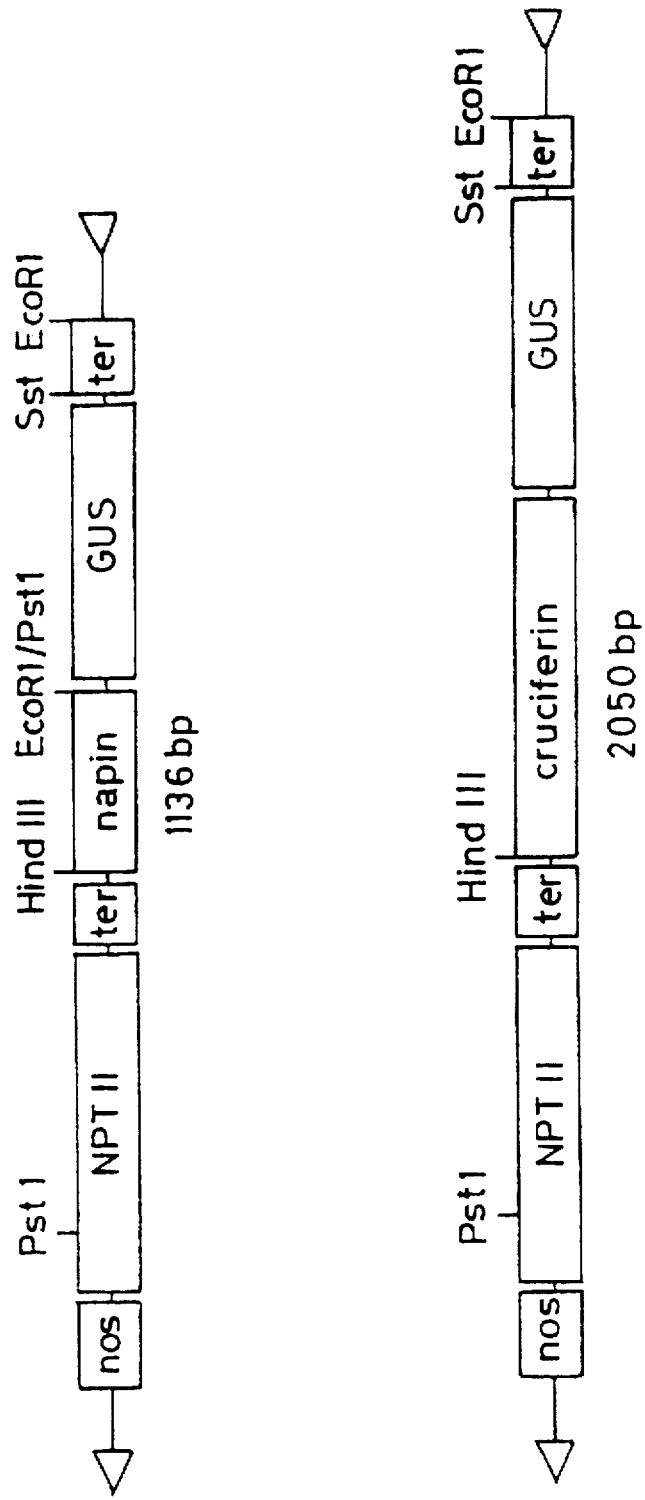
Figure 12:
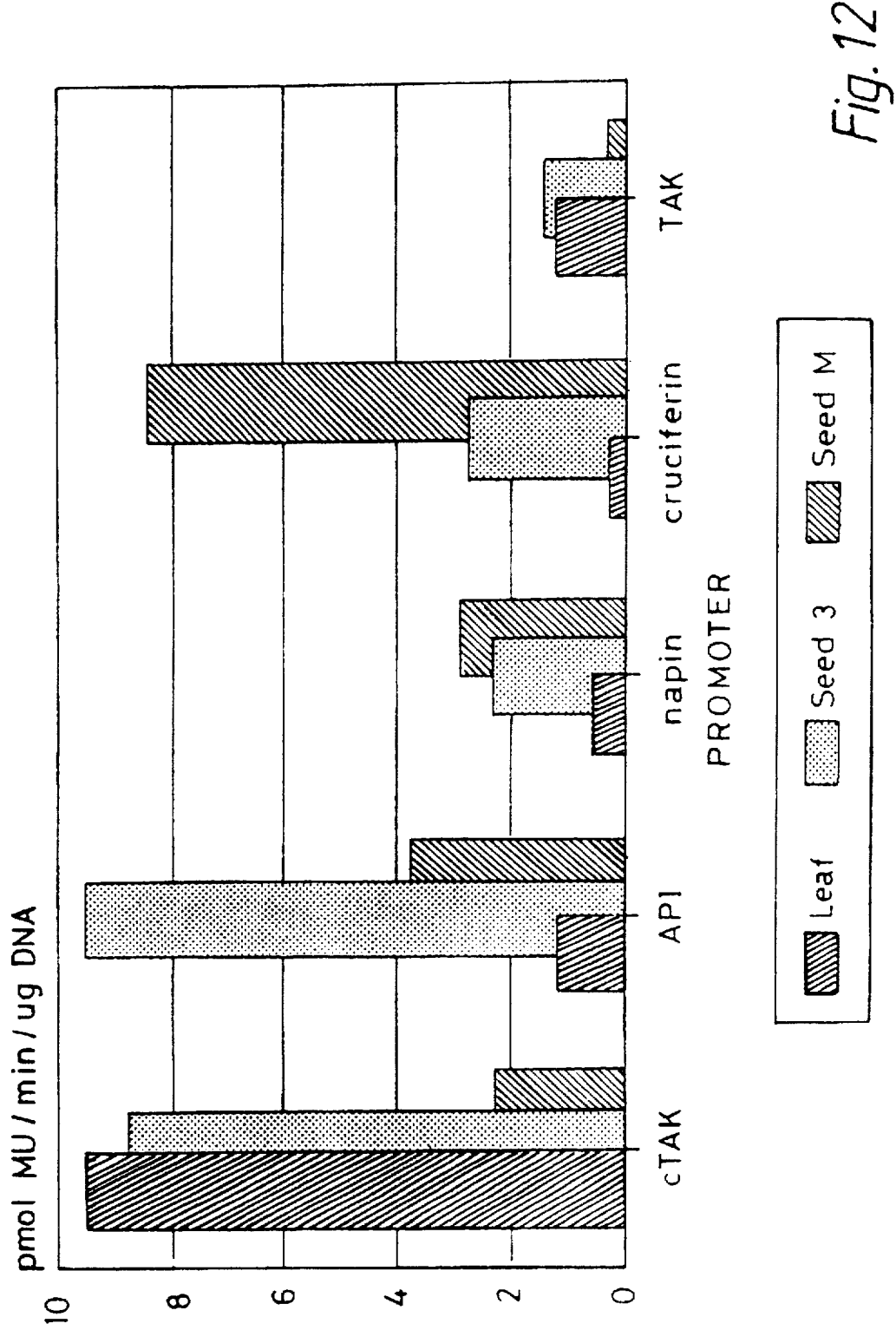

This shows the determined nucleotide sequence (2233 bp; SEQ ID NO:2) of the ACP05 genomic clone provided with the deduced amino acid sequence above the corresponding DNA sequence and the restriction enzyme sites indicated in FIG. 1 given in bold type letters and indicated below the DNA sequence.

Nucleotides 1–6 (SalI site) are the remainder of the M13 cloning vector described in Example 1.b, whereas polynucleotide 7–2233 originates from the ACP05 clone. Nucleotides 7–12 form the PstI restriction site CTGCAG. The AP2 promoter (0.29 kb) is the polynucleotide 640–930, thus starting with the BglII restriction site AGATCT and ending just before the start site of transcription, the first A in GGGCATCACG.

The introns are polynucleotides 1048–1317, 1426–1501 and 1625–1726.

Polynucleotides 1000–1047 (SEQ ID NO:3), and 1318–1422 encode the transit peptide −51 to −1 (Met Ser Thr . . . Val Ser Cys). Nucleotides 1423–1425 (SEQ ID NO:4), 1502–1624 (SEQ ID NO:5) and 1727–1849 (SEQ ID NO:6) encode the mature ACP 1 to 83 (Ala Ala Lys . . . Ala Lys Lys). Nucleotides 1850–1852 form the stop codon TGA.

FIG. 4

Construction of plant transformation vector pAP1GUS.

FIG. 5

Tobacco seed development. Relationship between days after flowering (DAF)=days post anthesis (dpa) and morphological stage of tobacco seeds.

FIG. 6

GUS (β-glucuronidase) activity in individual AP1GUS transgenic tobacco plants. GUS activities (pmol MU/minute/mg fresh weight) were measured in seed stages 1, 2 and 3 and leaf of plants transformed with pAP1GUS or pcTAK (control) vectors.

FIG. 7

GUS activity in AP1GUS transgenic tobacco plants.

Working out the seed/leaf values for individual plants obtained from 13 AP1GUS and 4 cTAK (control) transgenic plants and then averaging the figures obtained, the relative GUS activities (seed/leaf) for stages 1, 2 and 3 were calculated.

FIG. 8

Construction of plant transformation vector pAP2GUS.

FIG. 9

Construction of plant transformation vector pAP3GUS.

FIG. 10

GUS activity in AP1GUS, AP2GUS and AG3GUS transgenic tobacco plants. Average values (from 10 plants) of GUS activity (pmol MU/minute/μg DNA) of leaf, stage 3 seed and mature seed from AP1GUS, AP2GUS, AP3GUS plants and control TAK and cTAK plants.

FIG. 11

Transcriptional fusions between napin and cruciferin promoter sequences and the GUS structural gene, yielding plasmids PNAPGUS and pCRUGUS, respectively. The triangles at both sides indicate the left and right T-DNA borders.

FIG. 12

GUS activity in AP1GUS, NAPGUS, CRUGUS, cTAK and TAK transgenic tobacco plants. Average values (from 10 plants) of GUS activity (pmol MU/minute/μg DNA) of leaf, stage 3 seed and mature seed.

FIG. 13

Accumulation of lipid and protein during development of tobacco seed. Values (as % of fresh weight) are plotted as a percentage of the maximum recorded measurement.

FIG. 14

GUS activity (pmol MU/minute/mg fresh weight) through seed development of AP1GUS and CRUGUS transgenic tobacco plants.

FIG. 15

Figure 13:
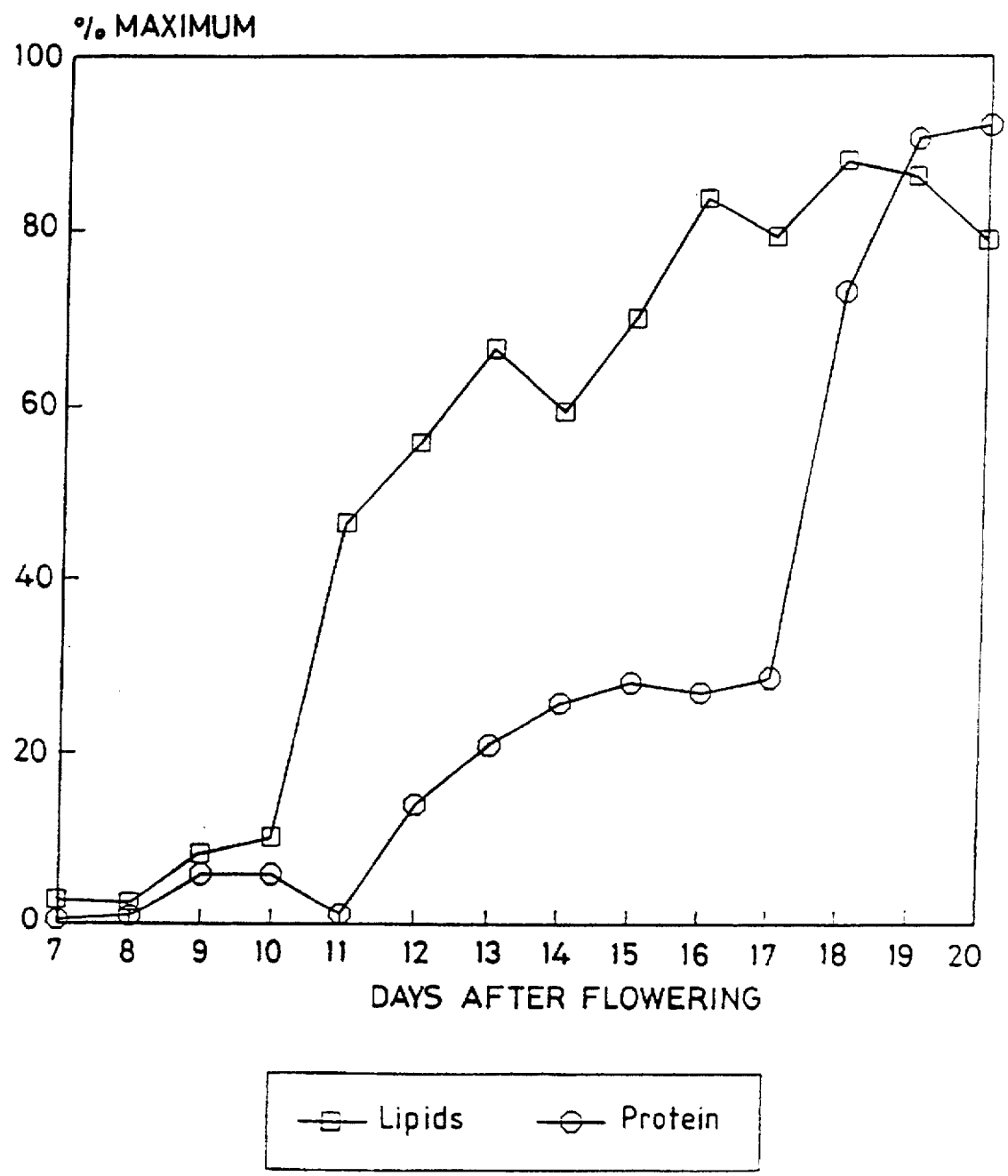
Figure 14:
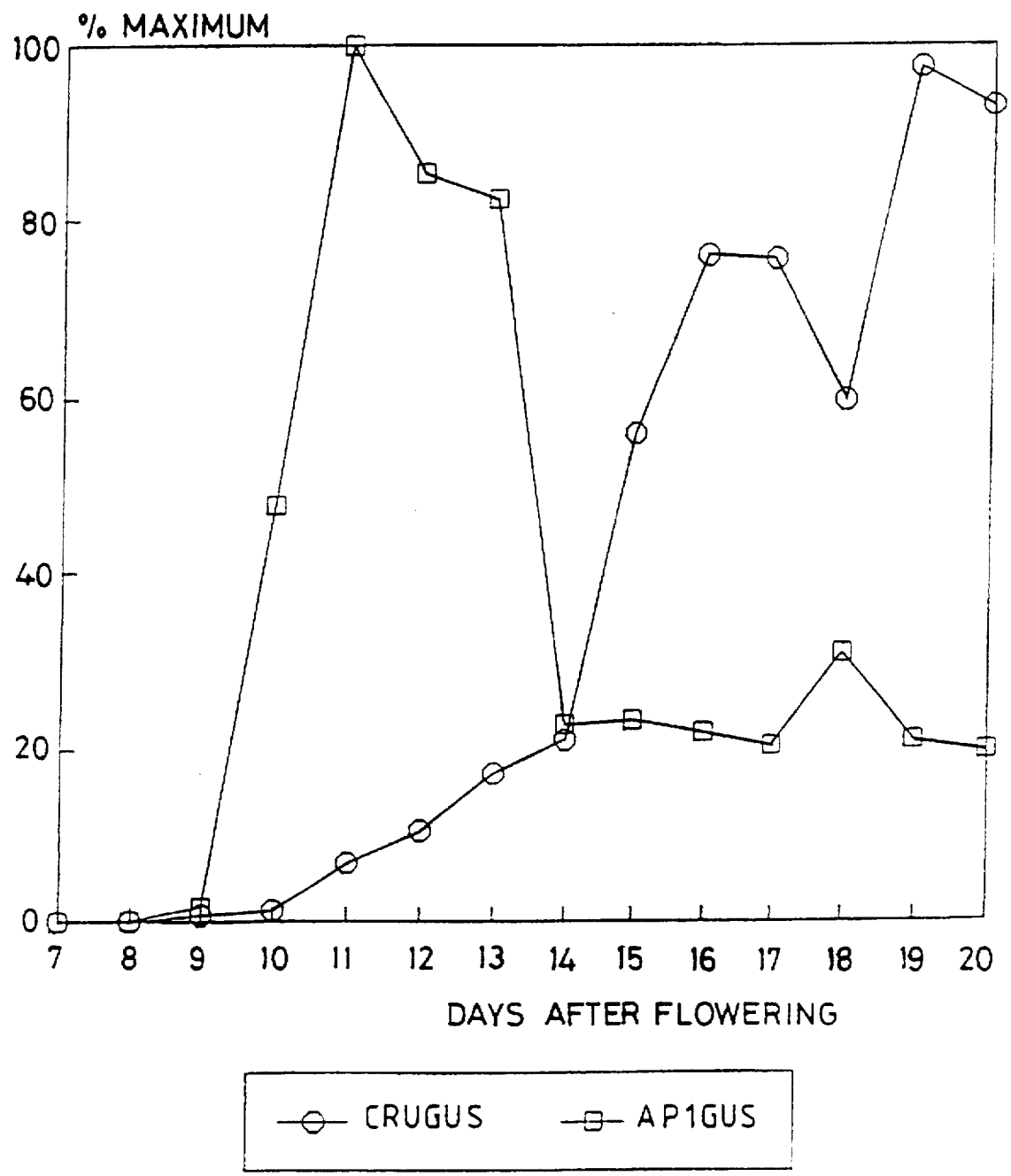
Figure 15:
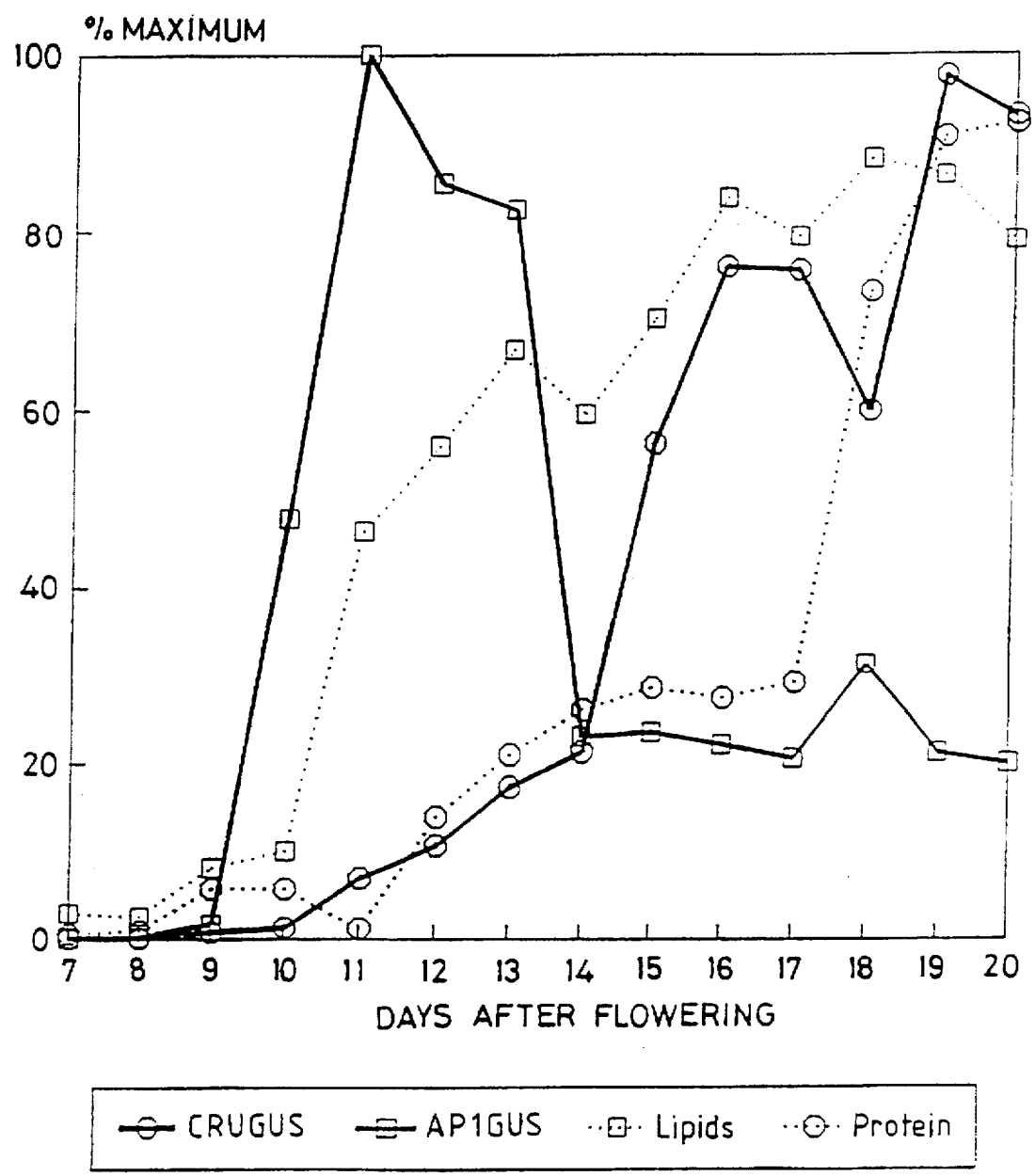
Figure 17:
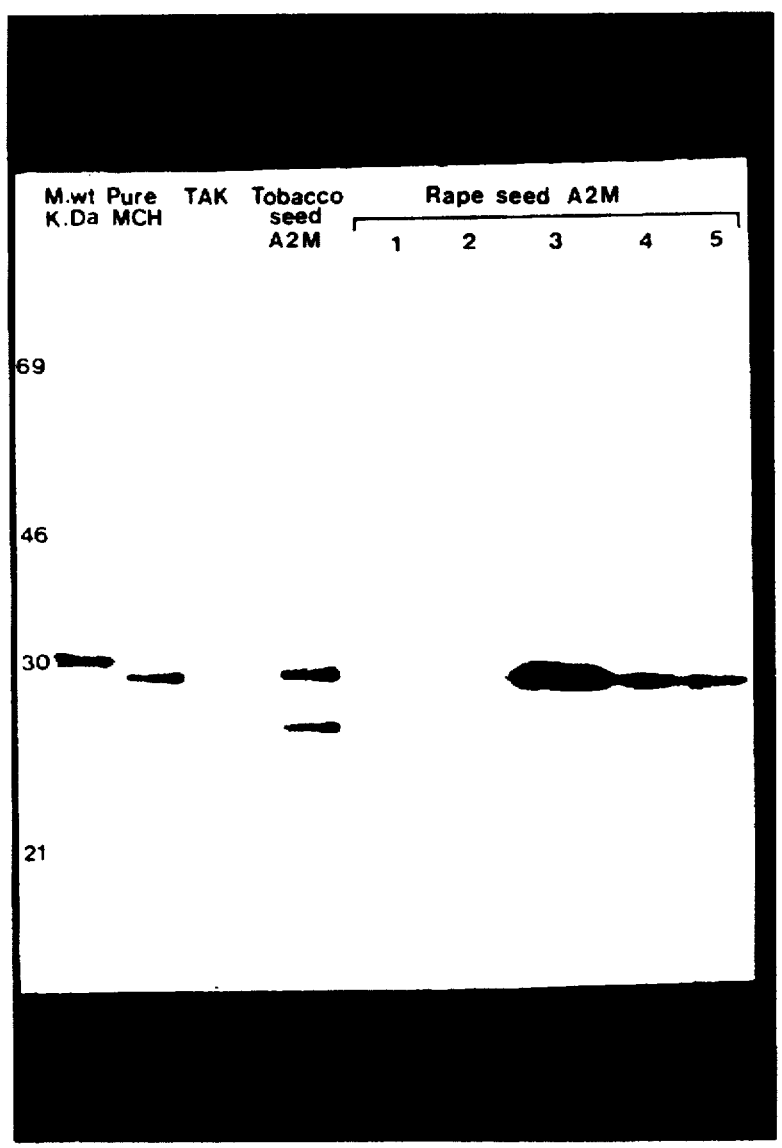

GUS activity measurements through seed development of APLGUS and CRUGUS transgenic tobacco plants superimposed upon accumulation of lipid and protein during seed development (i.e. FIGS. 13 and 14 combined).

FIG. 16 (1/4–4/4)

This shows the nucleotide sequence of a chimaeric construct containing the 1.4 kb AP1 promoter of which only the sequenced part is shown, i.e. the about 970 bp PstI-BglII fragment, an ACP transit sequence, almost the complete MCH gene, and part of the 3'-non-coding sequence of the MCH gene. The nucleotide sequence is provided with the deduced amino acid sequence above the corresponding DNA sequence and some relevant restriction enzyme sites are given in bold type letters and indicated below the DNA sequence (SEQ ID NO:7 and SEQ ID NO:8).

Thus polynucleotide 1–987 is identical to polynucleotide 7–993 of the DNA sequence of the ACP05 gene given in FIG. 3.

Polynucleotide 988–1149 originates from various chimaeric constructs and comprises the transit sequence of ACP cDNA clone 05E01 plus the first codon of the ACP structural gene (GCG encoding Ala). This ACP-originating part was connected to the MCH structural gene in which its ATG start codon was replaced by GCA encoding Ala Thus polynucleotide 1153–1938 encodes polypeptide 3–264 in FIG. 16 being identical to polypeptide 2–263 of the MCH protein. Codon 1939–1941 is the stop codon of the MCH structural gene. Polynucleotide 1942–2010 is part of the 3'-non-coding region of the MCH gene. Nucleotides 2011–2015 originate from the BglII site added for facilitating cloning of the DNA sequence.

FIG. 17

Figure 18:
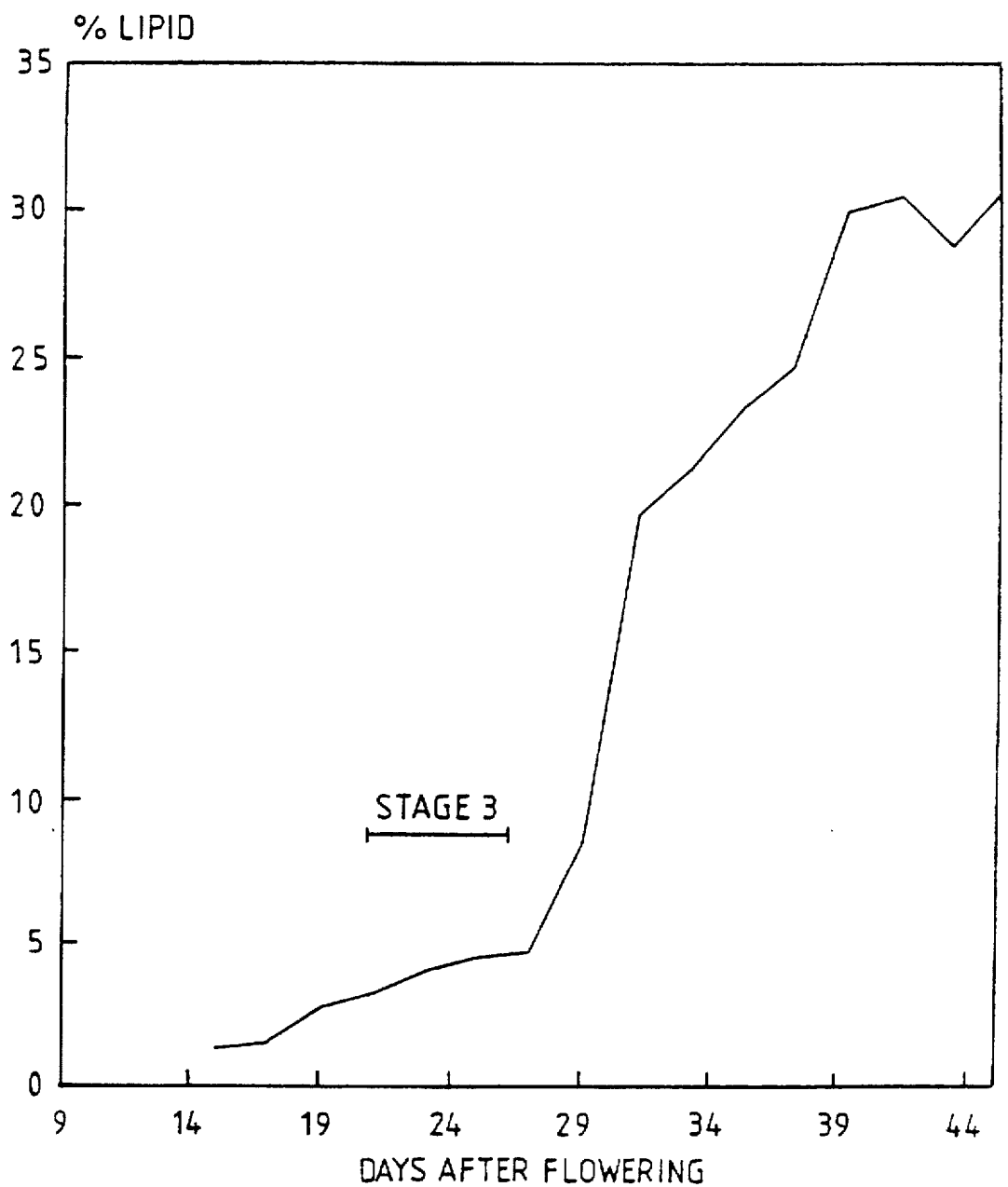

This autoradiograph shows the MCH expression by means of Western blot analysis with rape seed extracts at stages 1–5 of rape transformed with the pAP1A2M plasmid. It shows that MCH expression is barely detectable in stages 1 and 2, but a dramatic increase is observed during stage 3, just prior to the onset of storage lipid deposition in oil seed rape (see FIG. 18). The left hand site of the autoradiograph shows a molecular weight marker, pure MCH, an extract from plants transformed with PTAK as a control, and seed of tobacco transformed with the pAP1A2M plasmid.

FIG. 18

Lipid accumulation during rape seed development. The onset of storage lipid deposition in oil seed rape starts about 14 DAF, reaches a reasonable value between 19 and 27 DAF corresponding to stage 3 seed and increases dramatically after 29 DAF.

LITERATURE MENTIONED IN THE SPECIFICATION

European patent specification EP-A2-0255377 (CALGENE, INC.), published on 3 Feb. 1988 with claimed priority date of 31 Jul. 1986, European patent specification EP-A2-0255378 (CALGENE, INC.), published on 3 Feb. 1988 with claimed priority date of 31 Jul. 1986, An et al.; Binary vectors; In: Plant Molecular Biology Manual (edited by Galvin and Schilperoort) A3 (1988) 1–19

Barfield et al.; Plant Cell Reports 4 (1985) 104–107

Dellaporta; Plant Mol. Biol. Reporter 1 (1983) 19–21

R. J. Ellis & C. Robinson; In: Advances in Botanical Research 14 (1987/8) 1–24; published by Academic Press Ltd. (ISBN 0-12-005914-2)

Fry et al., Plant Cell Reports 6 (1987) 321–325

A. Hoekema et al.; Nature 303 (1983) 179–181

Holsters et al.; Mol. Gen. Genet. 163 (1978) 181–187

Horsch et al.; Science 227 (1985) 1229–1231

Jones et al.; EMBO J. 4 (1985) 2411–2418

V. C. Knauf; TIBTECH 5 (Feb 1987) 40–47; The application of genetic engineering to oilseed crops Laemmli, Nature 227 (1970) 680–685

Libertini and Smith; J. Biol. Chem. 253 (1978) 13931401;

T. Maniatis, E. F. Fritsch, & J. Sambrook; Molecular Cloning; Cold Spring Harbor Laboratory Publ. (1982).

T. Murishige & F. Skoog; Physiol. Plant 15 (1962) 473–497

Otten and Schilperoort, Biochem. Biophys. Acta 527 (1978) 497–500

M. A. Post-Beittenmiller et al.; The Plant Cell 1 (1989) 889–899

R. Safford et al.; Biochem. 26 (1987) 1358–1364;

R. Safford et al.; Eur. J. Biochem. 174 (1988) 287–295; Plastid-localised seed acyl-carrier protein of Brassica napus is encoded by a distinct, nuclear multigene family J. de Silva et al.; Plant Molecular Biology 14 (1990) 537–548; The isolation and sequence analysis of two seed-expressed acyl carrier protein genes from Brassica napus A. R. Slabas et al.; 7th International Symposium of the Structure and Function of Plant lipids, University of California, Davis, Calif., (1986);

P. K. Stumpf et al.; Fatty acid biosynthesis in higher plants; In: Fatty Acid Metabolism and Its Regulation; Elsevier Press, Amsterdam, Numa S. (ed), (1984) 155–179

G. Van den Broek et al.; Nature 313 (1985) 358–363;

J. D. Watson, J. Tooze & D. T. Kurtz; Chapter 13 (Genetic Engineering of Plants by Using Crown Gall Plasmids) on pages 164–175; In: Recombinant DNA, A Short Course, publ. Scientific American Books (1983) distr. W. H. Freeman and Company, New York. U.S.A.

Zambryski et al.; EMBO 2 (1983) 2143–2150

What is claimed is:

1. A recombinant DNA construct containing a promoter that is capable of acting as a seed-specific plant promoter, said promoter comprising at least the 291 bp polynucleotide of clone ACP05 given in the specification, comprising:

```
1
AGATCTGATT GGTAAGATAT GGGTACTGTT
                    TGGTTTATAT GTTTTGACTA  50
TTCAGTCACT ATGGCCCCCA TAAATTTTAA
                    TTCGGCTGGT ATGTCTCGGT 100
TAAGACCGGT TTGACATGGT TCATTTCAGT
                    TCAATTATGT GAATCTGGCA 150
CGTGATATGT TTACCTTCAC ACGAACATTA
                    GTAATGATGG GCTAATTTAA 200
GACTTAACAG CCTAGAAAGG CCCATCTTAT
                    TACGTAACGA CATCGTTTAG 250
AGTGCACCAA GCTTATAAAT GACGACGAGC
                    TACCTCGGGG C 291
``` and wherein said promoter controls the expression of a heterologous gene placed under control of said promoter.

2. A method of transforming plant cells, comprising:

(a) introducing into a transformable plant cell a DNA construct comprising the seed-specific promoter of claim 1 operably linked to a structural gene;

(b) growing the transformed plant cell to a whole plant.

3. A method of affecting the formation of vegetable seed oils, comprising:

(a) introducing into a transformable vegetable plant cell a DNA construct comprising the seed-specific promoter of claim 1 operably linked to a structural gene;

(b) growing the transformed plant cell via plantlet to a plant bearing seed; and (c) harvesting the resulting seed containing vegetable oil.

4. A plant cell transformed with a DNA construct containing the seed-specific promoter of claim 1.

5. A transgenic plant grown from a transformed plant cell according to claim 4.

6. A seed comprising the DNA construct of claim 1 produced by the plant of claim 5.

7. The seed according to claim 6, wherein said seed is of the Brassica family.

8. A process for producing a protein of interest in plant cells, which comprises expressing a structural gene encoding said protein, said plant cells containing a recombinant DNA construct according to claim 1 comprising said structural gene.

9. The process according to claim 8 wherein said is expressed.

10. The process according to claim 8, further comprising the step of isolating said protein from the plant cells.

11. A DNA construct according to claim 1, comprising at least the 1 kb PstI-BglII 5' upstream fragment of the rape ACP05 gene given in FIG. 1.

12. A DNA construct according to claim 1, comprising at least the 1.4 kb BamHI-BglII 5' upstream fragment of the rape ACP05 gene given in FIG. 1.

13. A DNA construct according to claim 1, comprising a seed-specific plant promoter present in plasmid pAP1GUS present in *E. coli* JM101/pAP1GUS (NCIMB 40396).

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 291 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 1:

-continued

| | | | | | |
|---|---|---|---|---|---|
| AGATCTGATT | GGTAAGATAT | GGGTACTGTT | TGGTTTATAT | GTTTTGACTA | TTCAGTCACT | 60
| ATGGCCCCCA | TAAATTTTAA | TTCGGCTGGT | ATGTCTCGGT | TAAGACCGGT | TTGACATGGT | 120
| TCATTTCAGT | TCAATTATGT | GAATCTGGCA | CGTGATATGT | TTACCTTCAC | ACGAACATTA | 180
| GTAATGATGG | GCTAATTTAA | GACTTAACAG | CCTAGAAAGG | CCCATCTTAT | TACGTAACGA | 240
| CATCGTTTAG | AGTGCACCAA | GCTTATAAAT | GACGACGAGC | TACCTCGGGG | C | 291

( 2 ) INFORMATION FOR SEQ ID NO: 2:

( i ) SEQUENCE CHARACTERISTICS:
        ( A ) LENGTH: 2233 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: 1000..1047

( i x ) FEATURE:
        ( A ) NAME/KEY: CDS
        ( B ) LOCATION: 1318..1425

( i x ) FEATURE:
        ( A ) NAME/KEY: CDS
        ( B ) LOCATION: 1502..1624

( i x ) FEATURE:
        ( A ) NAME/KEY: CDS
        ( B ) LOCATION: 1727..1848

( x i ) SEQUENCE DESCRIPTION: SEQ ID NO: 2:

| | | | | | |
|---|---|---|---|---|---|
| GTCGACCTGC | AGCCAGAAGG | ATAAAGAAAT | TTGGACGCC | TGAAGAAGAG | GCAGTTCTGA | 60
| GGGAAGGAGT | AAAAGAGTAT | GTCTCCTTAA | CTCTACTATC | AAGTTTCAAG | AAGCTGAGCT | 120
| TGGCTCTACC | TTGATATGTT | TATTGCTGTT | GTGCAGGTAT | GGTAAATCAT | GGAAAGAGAT | 180
| AAAGAATGCA | AACCCTGAAG | TATTCGCAGA | GAGGACTGAG | GTGAGAGAGC | ATGTCACTTT | 240
| TGTGTTACTC | ATCTGAATTA | TCTTATATGC | GAATTGTGAG | TGGTACTAAA | AAAGGTTGTA | 300
| ACTTTTGGTA | GGTTGATTTG | AAGGATAAAT | GGAGGAACTT | GGTTCGGTAG | CCGTAACAAG | 360
| TTTTTGGGAA | TCTCTTGGGT | TTTAAATTGC | TATGGAGTTT | TTTTTTGCCT | GCGTGACAAC | 420
| ATATCATCAG | CTGTTGAGAA | GGAAGATGGT | ATTAGAAAGG | GTCTTTCTTT | CACATTTTGT | 480
| GTTGTGGACA | AATATTAAAG | TCAAATGTGG | CACATGGATT | TTAATTCGGC | CGGTATGGTT | 540
| TGGTTAAGAC | TGGTTAACA | TGTATAATTA | GTCTTTGTTT | TATTGGCTC | AGCGGTTTGT | 600
| TGGTGTTGGT | TAGGAACTTA | GGCTTGTCTC | TTTCTGATAA | GATCTGATTG | GTAAGATATG | 660
| GGTACTGTTT | GGTTTATATG | TTTTGACTAT | TCAGTCACTA | TGGCCCCCAT | AAATTTTAAT | 720
| TCGGCTGGTA | TGTCTCGGTT | AAGACCGGTT | TGACATGGTT | CATTTCAGTT | CAATTATGTG | 780
| AATCTGGCAC | GTGATATGTT | TACCTTCACA | CGAACATTAG | TAATGATGGG | CTAATTTAAG | 840
| ACTTAACAGC | CTAGAAAGGC | CCATCTTATT | ACGTAACGAC | ATCGTTTAGA | GTGCACCAAG | 900
| CTTATAAATG | ACGACGAGCT | ACCTCGGGGC | ATCACGCTCT | TTGTACACTC | CGCCATCTCT | 960
| CTCTCCTTCG | AGCACAGATC | TCTCTCGTGA | ATATCGACA | ATG TCG ACC | ACT TTC | 1014
| | | | | Met Ser Thr | Thr Phe |
| | | | | 1 | 5 |
| TGC TCT TCC | GTC TCC ATG | CAA GCC ACT | TCT CTG GTA | TTA GAT C | ATT TTG CCTC | 1067

```
Cys Ser Ser Val Ser Met Gln Ala Thr Ser Leu
             10                  15

TGATCTGATT  CTTGCTGTTT  GTCACCGTTC  AAAACTCTCG  ACGCATGTTT  TGATTATGTT   1127

GAGAATTAGA  AAAATGTTAG  CTTTACGAAT  CTTTAGTGAT  CATTTCAATT  GGATTTGCAA   1187

TCCTGTGTGA  TCTGTATTCA  TTTGATCTG   TATTCATTTT  GAATCACAAC  TTGCGTGCGA   1247

GCTGTAATAG  TGTGATTGAG  TAGTAGTGTT  TTTGAATGAA  CATGTTTTGT  TGTATTGATG   1307

GAACAAACAG GCA GCA ACA ACG AGG ATT AGT TTC CAG AAG CCA GCT TTG          1356
           Ala Ala Thr Thr Arg Ile Ser Phe Gln Lys Pro Ala Leu
            1           5                   10

GTT TCA AGG ACT AAT CTC TCC TTC AAT CTA AGC CGT TCA ATC CCC ACT         1404
Val Ser Arg Thr Asn Leu Ser Phe Asn Leu Ser Arg Ser Ile Pro Thr
 15              20                  25

CGC CTC TCA GTC TCC TGC GCG GTATGTTCTT TTCTAACACC ACTCTCAGCA            1455
Arg Leu Ser Val Ser Cys Ala
 30              35

TTTGTTTCGA GATTCTTAA  GTTTTTGTCT  ATTTGGTTT  TATTAG GCC AAA CCA         1510
                                                    Ala Lys Pro
                                                     1

GAG ACA GTT GAG AAA GTG TCT AAG ATC GTC AAG AAG CAG CTA TCA CTC         1558
Glu Thr Val Glu Lys Val Ser Lys Ile Val Lys Lys Gln Leu Ser Leu
         5               10                  15

AAA GAC GAT CAA AAC GTC GTT GCG GAA ACC AAA TTT GCT GAT CTT GGA         1606
Lys Asp Asp Gln Asn Val Val Ala Glu Thr Lys Phe Ala Asp Leu Gly
 20              25                  30                  35

GCA GAT TCT CTC GAC ACT GTAATTCACC AAATGAATCA CTCTCTATGT                1654
Ala Asp Ser Leu Asp Thr
             40

GAATTAAACA  ACTTGTGTAG  TTTTTTTTTT  TTTTTTTTTT  AATACTGATT  AGATTGAGTG   1714

TTTGCATGC  AG GTT GAG ATA GTG ATG GGT TTA GAG GAA GAG TTT CAT           1762
              Val Glu Ile Val Met Gly Leu Glu Glu Glu Phe His
               1           5                   10

ATC GAA ATG GCT GAA GAA AAA GCA CAG AAG ATC ACA ACG GTG GAG GAA         1810
Ile Glu Met Ala Glu Glu Lys Ala Gln Lys Ile Thr Thr Val Glu Glu
         15                  20                  25

GCT GCT GAG CTC ATT GAT GAG CTC GTG CAA GCC AAGAAGTGAC TTTTAGTATT       1863
Ala Ala Glu Leu Ile Asp Glu Leu Val Gln Ala Lys
         30                  35              40

AAGAGAAGAA  CCAAAGGCTT  TGTTGTTTTC  ATAATCTTTC  TGTCATTTTC  TTTTATTATG   1923

ATGTCAAGTC  AAGCGACTCT  TTGCTAGTAA  TCTGTATGCC  ATGGATCTCT  CTCTCTATTT   1983

GTCGACTGAA  AACTTTTGGG  TTACACATGA  AAGCTTTTTC  TTTTCTAAA   ATCCAAAATG   2043

AAAGAGTTGT  ATTAACAGAT  ACATAAGTGA  AAGAGTAGTC  CCTAAGATGA  CACTAGCTTC   2103

ATTTATAAAC  AATCCTATCA  CATTGTATAT  ACAGGTTATG  ATTTATTCCC  AATCAGCGTC   2163

AAAGAATCCA  GCATCTTTCA  TCTCTGAATA  GTAGACATTC  TCCAAGTTTA  GATCTTCCTC   2223

CTCGATCAAA                                                              2233
```

( 2 ) INFORMATION FOR SEQ ID NO: 3:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 3:

Met Ser Thr Thr Phe Cys Ser Ser Val Ser Met Gln Ala Thr Ser Leu ( 2 ) INFORMATION FOR SEQ ID NO: 4:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
Ala Ala Thr Thr Arg Ile Ser Phe Gln Lys Pro Ala Leu Val Ser Arg
 1               5                  10                  15

Thr Asn Leu Ser Phe Asn Leu Ser Arg Ser Ile Pro Thr Arg Leu Ser
            20                  25                  30

Val Ser Cys Ala
            35
```

( 2 ) INFORMATION FOR SEQ ID NO: 5:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

```
Ala Lys Pro Glu Thr Val Glu Lys Val Ser Lys Ile Val Lys Lys Gln
 1               5                  10                  15

Leu Ser Leu Lys Asp Asp Gln Asn Val Val Ala Glu Thr Lys Phe Ala
            20                  25                  30

Asp Leu Gly Ala Asp Ser Leu Asp Thr
            35                  40
```

( 2 ) INFORMATION FOR SEQ ID NO: 6:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

```
Val Glu Ile Val Met Gly Leu Glu Glu Glu Phe His Ile Glu Met Ala
 1               5                  10                  15

Glu Glu Lys Ala Gln Lys Ile Thr Thr Val Glu Glu Ala Ala Glu Leu
            20                  25                  30

Ile Asp Glu Leu Val Gln Ala Lys
            35                  40
```

( 2 ) INFORMATION FOR SEQ ID NO: 7:

( i ) SEQUENCE CHARACTERISTICS:
        ( A ) LENGTH: 2015 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO

-continued ( i x ) FEATURE:
    ( A ) NAME/KEY: CDS
    ( B ) LOCATION: 994..1938

( x i ) SEQUENCE DESCRIPTION: SEQ ID NO: 7:

```
CTGCAGCCAG AAGGATAAAG AAATTTTGGA CGCCTGAAGA AGAGGCAGTT CTGAGGGAAG    60

GAGTAAAAGA GTATGTCTCC TTAACTCTAC TATCAAGTTT CAAGAAGCTG AGCTTGGCTC   120

TACCTTGATA TGTTTATTGC TGTTGTGCAG GTATGGTAAA TCATGGAAAG AGATAAAGAA   180

TGCAAACCCT GAAGTATTCG CAGAGAGGAC TGAGGTGAGA GAGCATGTCA CTTTTGTGTT   240

ACTCATCTGA ATTATCTTAT ATGCGAATTG TGAGTGGTAC TAAAAAAGGT TGTAACTTTT   300

GGTAGGTTGA TTTGAAGGAT AAATGGAGGA ACTTGGTTCG GTAGCCGTAA CAAGTTTTG    360

GGAATCTCTT GGGTTTTAAA TTGCTATGGA GTTTTTTTT GCCTGCGTGA CAACATATCA    420

TCAGCTGTTG AGAAGGAAGA TGGTATTAGA AAGGGTCTTT CTTCACATT TTGTGTTGTG    480

GACAAATATT AAAGTCAAAT GTGGCACATG GATTTTAATT CGGCCGGTAT GGTTTGGTTA   540

AGACTGGTTT AACATGTATA ATTAGTCTTT GTTTATTTG GCTCAGCGGT TTGTTGGTGT    600

TGGTTAGGAA CTTAGGCTTG TCTCTTTCTG ATAAGATCTG ATTGGTAAGA TATGGGTACT   660

GTTTGGTTTA TATGTTTTGA CTATTCAGTC ACTATGGCCC CCATAAATTT TAATTCGGCT   720

GGTATGTCTC GGTTAAGACC GGTTTGACAT GGTTCATTTC AGTTCAATTA TGTGAATCTG   780

GCACGTGATA TGTTTACCTT CACACGAACA TTAGTAATGA TGGGCTAATT TAAGACTTAA   840

CAGCCTAGAA AGGCCCATCT TATTACGTAA CGACATCGTT TAGAGTGCAC CAAGCTTATA   900

AATGACGACG AGCTACCTCG GGCATCACG CTCTTGTAC ACTCCGCCAT CTCTCTCTCC     960

TTCGAGCACA GATCTCTCTC GTGAATAACG AAA ATG GCG ACC ACT TTC AGC GCT  1014
                                     Met Ala Thr Thr Phe Ser Ala
                                      1               5

TCA GTC TCC ATG CAA GCT ACC TCT CTG GTC ACA ACA ACG AGG ATT AGT  1062
Ser Val Ser Met Gln Ala Thr Ser Leu Val Thr Thr Thr Arg Ile Ser
         10                  15                  20

TTC CAA AAG CCA GTT TTG GTT TCC AAC CAT GGA AGG ACT AAT CTC TCC  1110
Phe Gln Lys Pro Val Leu Val Ser Asn His Gly Arg Thr Asn Leu Ser
 25                  30                  35

TTC AAC CTA AGC CGC ACT CGC CTT TCA ATC TCT TGC GCG GCA GAG ACA  1158
Phe Asn Leu Ser Arg Thr Arg Leu Ser Ile Ser Cys Ala Ala Glu Thr
 40                  45                  50                  55

GCA GTC AAT GCT AAG AGT CCC AGG AAT GAA AAG GTT TTG AAC TGT TTG  1206
Ala Val Asn Ala Lys Ser Pro Arg Asn Glu Lys Val Leu Asn Cys Leu
                 60                  65                  70

TAT CAA AAT CCT GAT GCA GTT TTC AAG CTG ATC TGC TTC CCT TGG GCA  1254
Tyr Gln Asn Pro Asp Ala Val Phe Lys Leu Ile Cys Phe Pro Trp Ala
             75                  80                  85

GGA GGC GGC TCC ATC CAT TTT GCC AAG TGG GGC CAA AAG ATT AAC GAC  1302
Gly Gly Gly Ser Ile His Phe Ala Lys Trp Gly Gln Lys Ile Asn Asp
         90                  95                 100

TCT CTG GAA GTG CAT GCT GTA AGA CTG GCT GGA AGA GAA ACC CGA CTT  1350
Ser Leu Glu Val His Ala Val Arg Leu Ala Gly Arg Glu Thr Arg Leu
 105                 110                 115

GGA GAA CCT TTC GCA AAT GAC ATC TAC CAG ATA GCT GAT GAA ATC GTG  1398
Gly Glu Pro Phe Ala Asn Asp Ile Tyr Gln Ile Ala Asp Glu Ile Val
 120                 125                 130                 135

ACC GCC CTG TTG CCC ATC ATT CAG GAT AAA GCT TTT GCG TTT TTT GGC  1446
Thr Ala Leu Leu Pro Ile Ile Gln Asp Lys Ala Phe Ala Phe Phe Gly
                 140                 145                 150

CAC AGT TTT GGA TCC TAC ACT GCT CTT ATT ACT GCT CTG CTC CTA AAG  1494
His Ser Phe Gly Ser Tyr Thr Ala Leu Ile Thr Ala Leu Leu Leu Lys
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 155 |     |     |     |     | 160 |     |     |     |     | 165 |     |      |
| GAG | AAA | TAC | AAA | ATG | GAG | CCG | CTG | CAT | ATT | TTT | GTA | TCC | GGT | GCA | TCC | 1542 |
| Glu | Lys | Tyr<br>170 | Lys | Met | Glu | Pro<br> | Leu<br>175 | His | Ile | Phe | Val | Ser<br>180 | Gly | Ala | Ser |      |
| GCC | CCT | CAC | TCA | ACA | TCC | CGG | CCT | CAA | GTT | CCT | GAT | CTT | AAC | GAA | TTG | 1590 |
| Ala | Pro<br>185 | His | Ser | Thr | Ser | Arg<br>190 | Pro | Gln | Val | Pro | Asp<br>195 | Leu | Asn | Glu | Leu |      |
| ACA | GAA | GAA | CAA | GTC | AGA | CAT | CAC | CTT | CTG | GAT | TTC | GGA | GGC | ACG | CCC | 1638 |
| Thr<br>200 | Glu | Glu | Gln | Val | Arg<br>205 | His | His | Leu | Leu | Asp<br>210 | Phe | Gly | Gly | Thr | Pro<br>215 |      |
| AAG | CAT | CTC | ATA | GAA | GAC | CAG | GAT | GTT | CTG | AGG | ATG | TTC | ATT | CCT | TTG | 1686 |
| Lys | His | Leu | Ile | Glu<br>220 | Asp | Gln | Asp | Val | Leu<br>225 | Arg | Met | Phe | Ile | Pro<br>230 | Leu |      |
| CTG | AAG | GCA | GAT | GCT | GGC | GTT | GTG | AAA | AAA | TTC | ATC | TTT | GAC | AAG | CCC | 1734 |
| Leu | Lys | Ala | Asp<br>235 | Ala | Gly | Val | Val | Lys<br>240 | Lys | Phe | Ile | Phe | Asp<br>245 | Lys | Pro |      |
| TCC | AAA | GCT | CTT | CTC | TCT | CTG | GAC | ATA | ACG | GGC | TTC | CTT | GGA | TCT | GAA | 1782 |
| Ser | Lys | Ala<br>250 | Leu | Leu | Ser | Leu | Asp<br>255 | Ile | Thr | Gly | Phe | Leu<br>260 | Gly | Ser | Glu |      |
| GAT | ACA | ATA | AAG | GAC | ATA | GAA | GGC | TGG | CAA | GAC | CTA | ACC | AGT | GGG | AAG | 1830 |
| Asp | Thr<br>265 | Ile | Lys | Asp | Ile | Glu<br>270 | Gly | Trp | Gln | Asp | Leu<br>275 | Thr | Ser | Gly | Lys |      |
| TTT | GAT | GTC | CAC | ATG | CTG | CCA | GGC | GAC | CAC | TTT | TAT | CTG | ATG | AAG | CCC | 1878 |
| Phe<br>280 | Asp | Val | His | Met | Leu<br>285 | Pro | Gly | Asp | His | Phe<br>290 | Tyr | Leu | Met | Lys | Pro<br>295 |      |
| GAC | AAC | GAG | AAC | TTT | ATC | AAG | AAC | TAC | ATA | GCC | AAG | TGC | TTG | GAA | CTC | 1926 |
| Asp | Asn | Glu | Asn | Phe<br>300 | Ile | Lys | Asn | Tyr | Ile<br>305 | Ala | Lys | Cys | Leu | Glu<br>310 | Leu |      |
| TCG | TCA | CTC | ACT | TGACTACTTT | | TAGATGAGCT | | TTCTTTGGGG | | CTGTGGATAT | | | | | | 1978 |
| Ser | Ser | Leu | Thr<br>315 | | | | | | | | | | | | | |
| GCAGACGGTT | | CAAAAGCTGC | | TCCTCTGGGT | | CCAGATC | | | | | | | | | | 2015 |

( 2 ) INFORMATION FOR SEQ ID NO: 8:

( i ) SEQUENCE CHARACTERISTICS:
        ( A ) LENGTH: 315 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

| Met<br>1 | Ala | Thr | Thr | Phe<br>5 | Ser | Ala | Ser | Val | Ser<br>10 | Met | Gln | Ala | Thr | Ser<br>15 | Leu |
|---|---|---|---|---|---|---|---|---|---|---|---|---|---|---|---|
| Val | Thr | Thr | Thr<br>20 | Arg | Ile | Ser | Phe | Gln<br>25 | Lys | Pro | Val | Leu | Val<br>30 | Ser | Asn |
| His | Gly | Arg<br>35 | Thr | Asn | Leu | Ser | Phe<br>40 | Asn | Leu | Ser | Arg | Thr<br>45 | Arg | Leu | Ser |
| Ile | Ser<br>50 | Cys | Ala | Ala | Glu | Thr<br>55 | Ala | Val | Asn | Ala | Lys<br>60 | Ser | Pro | Arg | Asn |
| Glu<br>65 | Lys | Val | Leu | Asn | Cys<br>70 | Leu | Tyr | Gln | Asn | Pro<br>75 | Asp | Ala | Val | Phe | Lys<br>80 |
| Leu | Ile | Cys | Phe | Pro<br>85 | Trp | Ala | Gly | Gly | Ser<br>90 | Ile | His | Phe | Ala | Lys<br>95 |  |
| Trp | Gly | Gln | Lys | Ile<br>100 | Asn | Asp | Ser | Leu | Glu<br>105 | Val | His | Ala | Val | Arg<br>110 | Leu |
| Ala | Gly | Arg<br>115 | Glu | Thr | Arg | Leu | Gly<br>120 | Glu | Pro | Phe | Ala | Asn<br>125 | Asp | Ile | Tyr |

-continued

| | | | | | | | | | | | | | | |
|---|---|---|---|---|---|---|---|---|---|---|---|---|---|---|
| Gln | Ile | Ala | Asp | Glu | Ile | Val | Thr | Ala | Leu | Leu | Pro | Ile | Ile | Gln | Asp |
| | 130 | | | | | 135 | | | | | 140 | | | | |
| Lys | Ala | Phe | Ala | Phe | Phe | Gly | His | Ser | Phe | Gly | Ser | Tyr | Thr | Ala | Leu |
| 145 | | | | | 150 | | | | | 155 | | | | | 160 |
| Ile | Thr | Ala | Leu | Leu | Leu | Lys | Glu | Lys | Tyr | Lys | Met | Glu | Pro | Leu | His |
| | | | | 165 | | | | | 170 | | | | | 175 | |
| Ile | Phe | Val | Ser | Gly | Ala | Ser | Ala | Pro | His | Ser | Thr | Ser | Arg | Pro | Gln |
| | | | 180 | | | | | 185 | | | | | 190 | | |
| Val | Pro | Asp | Leu | Asn | Glu | Leu | Thr | Glu | Glu | Gln | Val | Arg | His | His | Leu |
| | | 195 | | | | | 200 | | | | | 205 | | | |
| Leu | Asp | Phe | Gly | Gly | Thr | Pro | Lys | His | Leu | Ile | Glu | Asp | Gln | Asp | Val |
| | 210 | | | | | 215 | | | | | 220 | | | | |
| Leu | Arg | Met | Phe | Ile | Pro | Leu | Leu | Lys | Ala | Asp | Ala | Gly | Val | Val | Lys |
| 225 | | | | | 230 | | | | | 235 | | | | | 240 |
| Lys | Phe | Ile | Phe | Asp | Lys | Pro | Ser | Lys | Ala | Leu | Leu | Ser | Leu | Asp | Ile |
| | | | | 245 | | | | | 250 | | | | | 255 | |
| Thr | Gly | Phe | Leu | Gly | Ser | Glu | Asp | Thr | Ile | Lys | Asp | Ile | Glu | Gly | Trp |
| | | | 260 | | | | | 265 | | | | | 270 | | |
| Gln | Asp | Leu | Thr | Ser | Gly | Lys | Phe | Asp | Val | His | Met | Leu | Pro | Gly | Asp |
| | | 275 | | | | | 280 | | | | | 285 | | | |
| His | Phe | Tyr | Leu | Met | Lys | Pro | Asp | Asn | Glu | Asn | Phe | Ile | Lys | Asn | Tyr |
| | 290 | | | | | 295 | | | | | 300 | | | | |
| Ile | Ala | Lys | Cys | Leu | Glu | Leu | Ser | Ser | Leu | Thr | | | | | |
| 305 | | | | | 310 | | | | | 315 | | | | | |